US010898706B2

(12) United States Patent
Pradeep

(10) Patent No.: US 10,898,706 B2
(45) Date of Patent: Jan. 26, 2021

(54) SYSTEMS, METHODS, AND DEVICES FOR BRAIN STIMULATION AND MONITORING

(71) Applicant: StimScience Inc., Berkeley, CA (US)

(72) Inventor: Anantha K. Pradeep, Piedmont, CA (US)

(73) Assignee: STIMSCIENCE INC., Berkeley, CA (US)

( * ) Notice: Subject to any disclaimer, the term of this patent is extended or adjusted under 35 U.S.C. 154(b) by 169 days.

(21) Appl. No.: 16/173,584

(22) Filed: Oct. 29, 2018

(65) Prior Publication Data

US 2019/0126033 A1   May 2, 2019

Related U.S. Application Data

(60) Provisional application No. 62/579,289, filed on Oct. 31, 2017.

(51) Int. Cl.
*A61N 1/05* (2006.01)
*A61N 1/36* (2006.01)
(Continued)

(52) U.S. Cl.
CPC ............ *A61N 1/0534* (2013.01); *A61B 5/048* (2013.01); *A61B 5/4812* (2013.01);
(Continued)

(58) Field of Classification Search
CPC ..... A61B 5/048; A61B 5/4812; A61B 5/4836; A61N 1/0531; A61N 1/0534; A61N 1/08;
(Continued)

(56) References Cited

U.S. PATENT DOCUMENTS

2015/0066104 A1\* 3/2015 Wingeier ............. A61B 5/4836
607/45
2016/0256105 A1\* 9/2016 Boyle ................ A61N 1/36014
(Continued)

OTHER PUBLICATIONS

Roy Cox, et al., "Individual Differences in Frequency and Topography of Slow and Fast Sleep Spindles, Frontiers in Human Neuroscience," www.frontiersin.org, Sep. 22, 2017, vol. 11, Article 433, 22 pages.

*Primary Examiner* — Carl H Layno
*Assistant Examiner* — Jane C Kalinock
(74) *Attorney, Agent, or Firm* — Kwan & Olynick LLP

(57) ABSTRACT

Provided are systems, methods, and devices for brain stimulation and monitoring. Brain stimulation may be provided to enhance slow wave and spindle synchrony. Such stimulation may provide increased memory consolidation. Furthermore, brain stimulation modalities may provide enhanced sleep and awakening. For example, transcranial direct current stimulation of the brain stimulation may enhance sleep quality. Moreover, one or more markers characterizing unconsciousness are may be identified based on changes in measured power densities or spectra. Further still, the above described modalities of brain stimulation may be implemented in an open-loop or closed loop manner. Brain state parameters may be generated for building models of the brain based on determined synchrony patterns between slow waves and spindles. The models may be used to determine a mediation procedure for adjusting the intensity of slow wave oscillations to enhance slow wave and spindle synchrony.

17 Claims, 17 Drawing Sheets
(12 of 17 Drawing Sheet(s) Filed in Color)

(51) Int. Cl.
*A61B 5/00* (2006.01)
*A61B 5/048* (2006.01)
*A61N 1/08* (2006.01)

(52) U.S. Cl.
CPC ........ *A61B 5/4836* (2013.01); *A61N 1/36025* (2013.01); *A61N 1/36078* (2013.01); *A61N 1/36092* (2013.01); *A61N 1/36139* (2013.01); *A61N 1/0531* (2013.01); *A61N 1/08* (2013.01)

(58) Field of Classification Search
CPC ............ A61N 1/36024; A61N 1/36078; A61N 1/36092; A61N 1/36139
USPC ........................................................ 607/116
See application file for complete search history.

(56) References Cited

U.S. PATENT DOCUMENTS

| | | | |
|---|---|---|---|
| 2018/0092600 A1* | 4/2018 | Simons | A61B 5/6803 |
| 2018/0140249 A1* | 5/2018 | Frohlich | A61B 5/7253 |
| 2019/0076046 A1* | 3/2019 | Pradeep | A61B 5/0478 |
| 2019/0125255 A1* | 5/2019 | Pradeep | A61B 5/4094 |
| 2019/0150768 A1* | 5/2019 | Pradeep | G16H 20/30 |
| 2020/0155061 A1* | 5/2020 | Pradeep | A61B 5/4064 |

\* cited by examiner

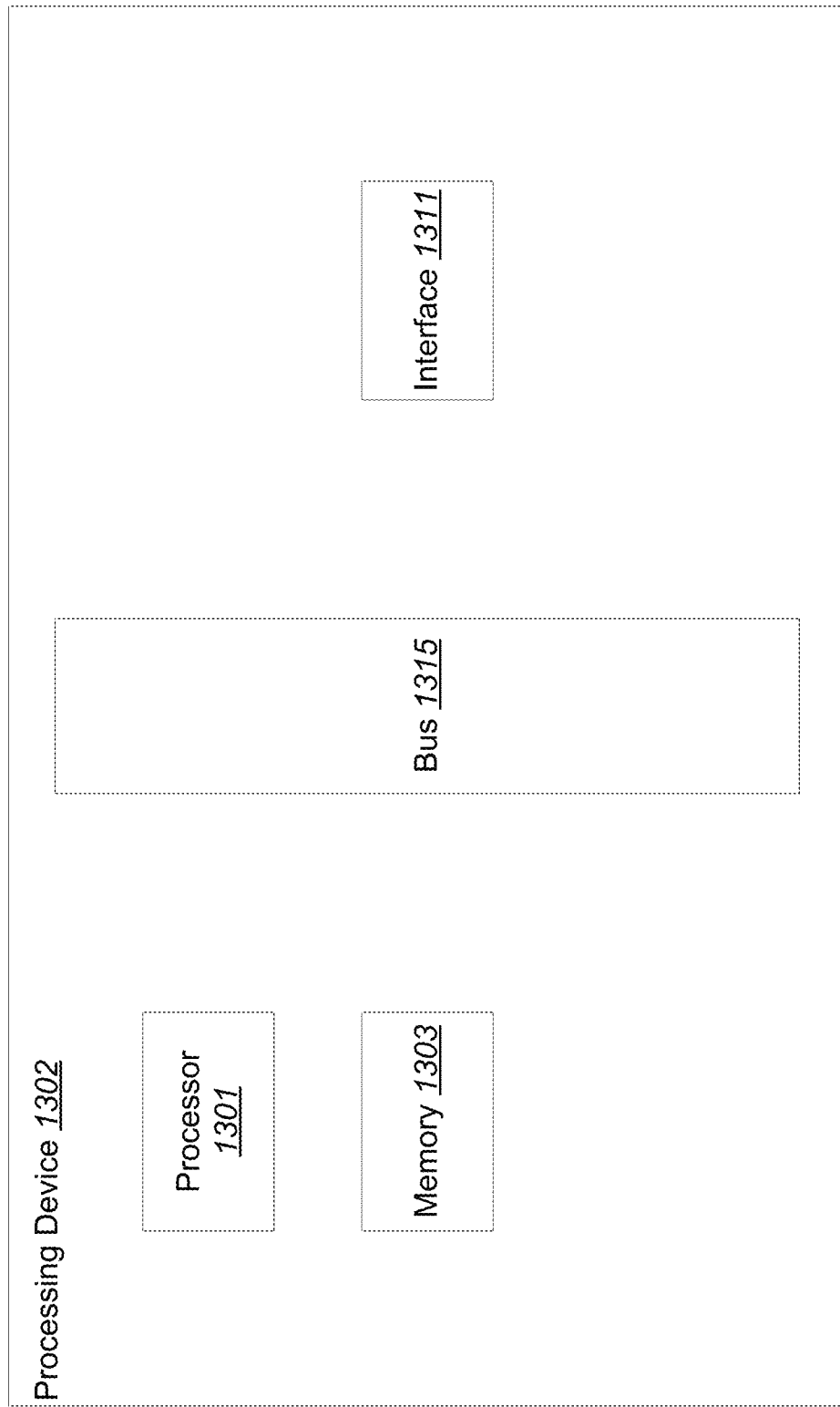

SYSTEMS, METHODS, AND DEVICES FOR BRAIN STIMULATION AND MONITORING

CROSS-REFERENCE TO RELATED APPLICATIONS

This application claims priority under 35 U.S.C. § 119(e) to U.S. Provisional Application No. 62/579,289, filed Oct. 31, 2017, entitled SYSTEMS, METHODS, AND DEVICES FOR BRAIN STIMULATION AND MONITORING, the contents of each of which are hereby incorporated by reference.

TECHNICAL FIELD

The present disclosure relates to mechanisms and processes directed to stimulation and monitoring associated with brain activity.

DESCRIPTION OF RELATED ART

A human brain may include neurons which exhibit measurable electrical signals when active. Accordingly, various measuring modalities, such as electrodes, may be used to measure such electrical activity. The neural activity of neurons may include many a variety of frequency components. Accordingly, such electrical activity may be measured and represented as a power spectrum in a frequency domain. Moreover, different behaviors or patterns in different frequency bands may be identified and referred to as particular types of waves, such as delta and theta waves.

SUMMARY

Provided are systems, methods, and devices for closed loop control associated with brain activity.

In various embodiments, systems, methods, and devices are provided for brain stimulation and monitoring. Brain stimulation may be provided to enhance slow wave and spindle synchrony. Such stimulation may provide increased memory consolidation. Furthermore, brain stimulation modalities may provide enhanced sleep and awakening. For example, transcranial direct current stimulation of the brain stimulation may enhance sleep quality. Moreover, one or more markers characterizing unconsciousness are may be identified based on changes in measured power densities or spectra. Further still, the above described modalities of brain stimulation may be implemented in an open-loop or closed loop manner.

In one aspect, methods may comprise obtaining a plurality of measurements from a brain of a user via an interface. The plurality of measurements may include indications of slow wave oscillations and sleep spindles. The methods may further comprise generating, via a first processing device comprising one or more processors, a plurality of brain state parameters characterizing one or more features of at least one brain state of the brain of the user. The brain state parameters may include an indication of a synchrony pattern between the measured slow wave oscillations and the measured sleep spindles.

The methods may further comprise, via a second processing device comprising one or more processors, generating a model of the brain of the user based, at least in part, on the plurality of measurements and the synchrony pattern; and determining, using the model of the brain of the user and training data comprising one or more mediation data points, a procedure for mediation configured to adjust the intensity of slow wave oscillations.

The methods may further comprise generating one or more control signals, via a controller, based on the procedure for mediation. The one or more control signals are transmitted to the interface.

The methods may further comprise generating, via the interface, one or more stimuli based on the one or more control signals. The one or more stimuli may be configured to increase slow wave oscillation power of the brain. The methods may further comprise applying the one or more stimuli to cortical tissue of the brain.

In some embodiments, the one or more stimuli is configured to enhance slow wave oscillation and spindle synchrony. In some embodiments, the at least one brain state includes an unconscious state corresponding to non-rapid-eye-movement sleep.

In some embodiments, generating a plurality of brain state parameters includes assessing a temporal directionality of interactions between the measured slow wave oscillations and sleep spindles.

In some embodiments, the methods may further comprise providing the procedure for mediation to one or more entities. Such one or more entities includes a client device corresponding to a medical professional.

Other implementations of this disclosure include corresponding devices, systems, and computer programs configured to perform the described methods. These other implementations may each optionally include one or more of the following features. For instance, provided systems may comprise an interface configured to obtain a plurality of measurements from a brain of a user. The plurality of measurements may include indications of slow wave oscillations and sleep spindles.

The systems may further comprise a first processing device comprising one or more processors configured to generate a plurality of brain state parameters characterizing one or more features of at least one brain state of the brain of the user. The brain state parameters may include an indication of a synchrony pattern between the measured slow wave oscillations and the measured sleep spindles.

The systems may further comprise a second processing device comprising one or more processors configured to: generate a model of the brain of the user based, at least in part, on the plurality of measurements and the synchrony pattern; and determine, using the model of the brain of the user and training data comprising one or more mediation data points, a procedure for mediation configured to adjust the intensity of slow wave oscillations. The systems may further comprise a controller comprising one or more processors configured to generate one or more control signals based on the procedure for mediation. The one or more control signals are transmitted to the interface.

This and other embodiments are described further below with reference to the figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 13 illustrates an example of a computer system capable of implementing various processes described in the present disclosure.

DETAILED DESCRIPTION OF EXAMPLE EMBODIMENTS

Figure 1A:
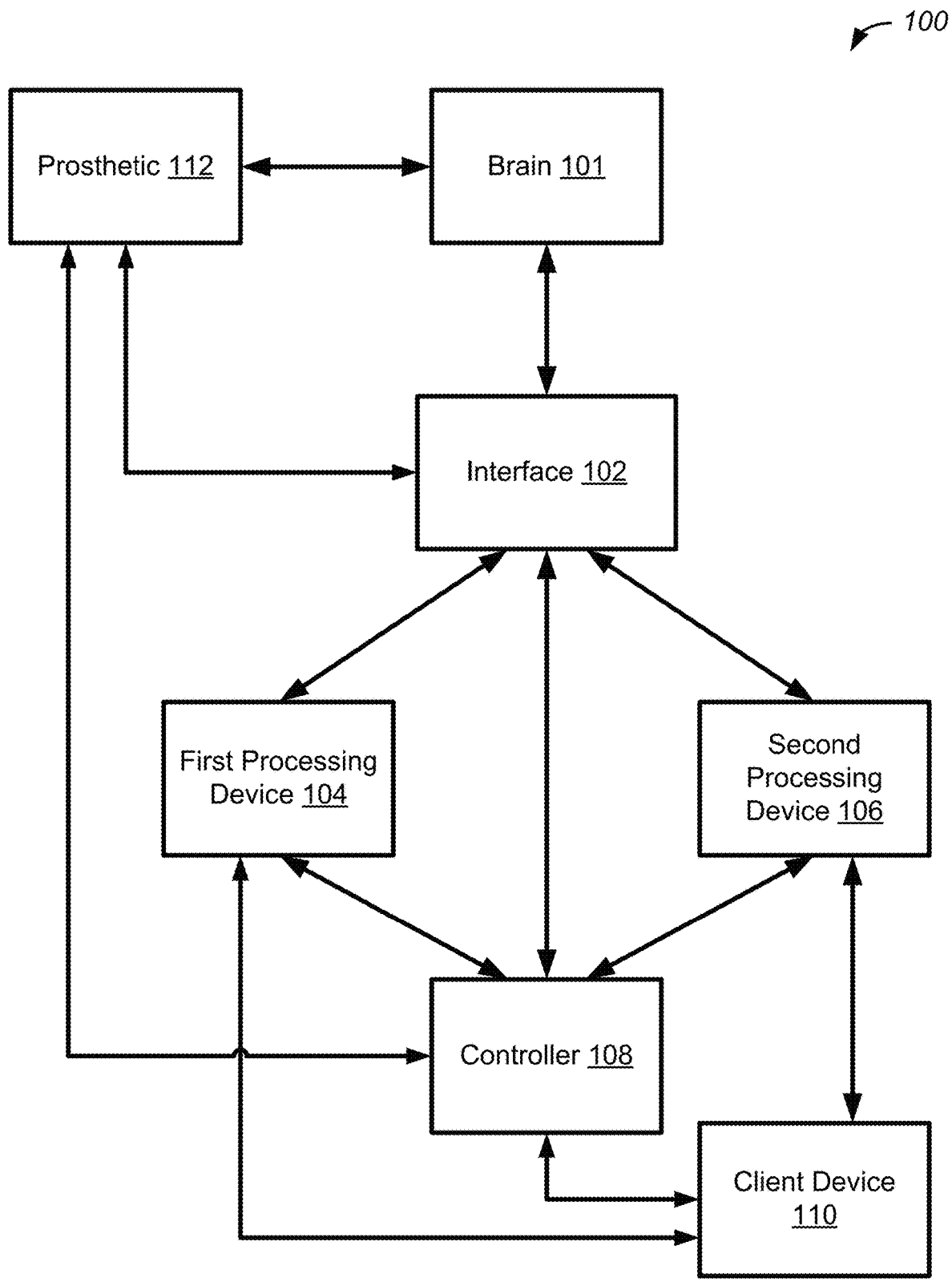
FIG. 1A illustrates an example of a system for monitoring and stimulating brain activity, configured in accordance with some embodiments.

Reference will now be made in detail to some specific examples of the invention including the best modes contemplated by the inventors for carrying out the invention. Examples of these specific embodiments are illustrated in the accompanying drawings. While the present disclosure is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In addition, although many of the components and processes are described below in the singular for convenience, it will be appreciated by one of skill in the art that multiple components and repeated processes can also be used to practice the techniques of the present disclosure.

In the following description, numerous specific details are set forth in order to provide a thorough understanding of the present invention. Particular embodiments of the present invention may be implemented without some or all of these specific details. In other instances, well known process operations have not been described in detail in order not to unnecessarily obscure the present invention.

According to embodiments disclosed herein, brain stimulation may be provided to enhance slow wave and spindle synchrony. As will be discussed in greater detail below, such stimulation may provide increased memory consolidation. More specifically, such stimulation may be provided to enhance slow wave, or delta bursts, and spindle synchrony during a state of sleep. Increases in such synchrony during sleep may enhance memory consolidation that normally occurs during sleep. Accordingly, embodiments disclosed herein relate to delta burst coupling with spindles, and how this is disrupted in aging.

Furthermore, according to embodiments described herein, brain stimulation modalities are disclosed for enhanced sleep and awakening. For example, transcranial direct current stimulation of the brain stimulation may enhance sleep quality. More specifically, when such stimulation is provided pre-sleep, the quality of sleep may be improved. In this way, embodiments disclosed herein provide stim enhanced sleep and faster awakening.

In embodiments disclosed herein, one or more markers characterizing unconsciousness are disclosed. Such a marker may be a universal marker. This marker may be used to identify unconsciousness when a subject or patient is either asleep or under anesthesia. In various embodiments, the marker may be identified based on a change in the 1/f slope for power between 30-60 Hz. Accordingly, changes in measured power densities or spectra may be utilized to identify a marker or parameter that characterizes a state of unconsciousness. Such techniques may be used for other types of monitoring as well.

In various embodiments, the above described modalities of brain stimulation may be implemented in an open-loop or closed loop manner. Accordingly, brain stimulation may be provided such that stimulation is provided independent of an output, and according to a designated stimulation protocol. In various embodiments, brain stimulation may be provided in a closed-loop manner in which stimulation is provided and modified based on measurements and changes in a subject's neural activity. Accordingly, the above-mentioned stimulation modalities may be modified and refined based on neural and behavioral measurements of a subject.

In various embodiments, the coupled interaction between slow wave oscillations and sleep spindles during non-rapid-eye-movement (NREM) sleep has been proposed to support memory consolidation. However, little evidence in humans supports this theory. Moreover, whether such dynamic coupling is impaired as a consequence of brain aging in later life, contributing to cognitive and memory decline, is unknown. Combining, electroencephalography (EEG), structural MRI and sleep-dependent memory assessment, these questions were addressed in cognitively normal young and older adults. Directional cross-frequency coupling analyses demonstrated that the slow wave governs a precise temporal coordination of sleep spindles, the quality of which predicts overnight memory retention. Moreover, selective atrophy within the medial frontal cortex in older adults predicted a temporal dispersion of this slow wave-spindle coupling, impairing overnight memory consolidation leading to forgetting. Prefrontal dependent deficits in the spatiotemporal coordination of NREM sleep oscillations provide a novel pathway to age-related memory decline.

The precise temporal coordination of NREM sleep oscillations has been proposed to support the long-term consolidation of memory. Within these theoretical frameworks, temporal interactions between cortical slow oscillations ("SO"; <1.25 Hz), sleep spindles (~12-16 Hz), and hippocampal ripples (~80-100 Hz) form a hierarchy that allows for information transformation necessary for long-term memory retention. In particular, the depolarizing 'up-states' of the SO are proposed to facilitate sleep spindle and ripple expression, with hippocampal ripples being temporally nested into spindle troughs. The coupling of these NREM oscillations is thought to support intrinsically timed information transfer across several spatiotemporal scales underlying long-term memory.

There is, however, limited empirical evidence supporting this oscillatory interaction model of hippocampal memory consolidation. Non-invasive brain stimulation findings have demonstrated that boosting SO power can indirectly co-modulate sleep spindle activity, while SO-spindle coupling during a nap in young adults tracks offline memory retention. Yet the mechanistic relationship of SO-spindle synchrony, and how this determines the success or failure of overnight hippocampal-dependent memory consolidation remains unknown, as does the causal necessity of brain regions in supporting coupled NREM oscillation dynamics and memory benefit.

Regarding the latter, there is growing evidence that aging markedly disrupts sleep and overnight memory consolidation. If sleep oscillatory coupling is compromised in older adults, what is it about the aging brain that degrades interactive synchrony of NREM oscillations leading to memory impairment? This question is of special relevance as it may reveal a currently under-appreciated mechanism (impaired SO-spindle coupling) that contributes to cognitive memory decline in later life, and if identified, would defined a novel therapeutic target for clinical intervention.

These unanswered questions were addressed by combining structural MRI, polysomnography with full-head (19 channel) scalp electroencephalography (EEG), and the assessment of sleep-dependent hippocampal memory, in young and older adults. Specifically tested was the hypothesis that the precise temporal coupling of cortical NREM SO-spindles, as predicted by theoretical models, facilitates overnight memory retention in young adults, and whether older adults have a temporal un-coupling of these oscillations leading to impaired overnight memory. Moreover, based on evidence in young and older adults demonstrating that the structural grey-matter morphology of the medial prefrontal cortex (mPFC) is associated with the quality of SO, and that this same mPFC region is an EEG source generator of SO linked to spindles, the hypothesis that structural grey matter integrity of mPFC predicts the degree of compromised SO-spindle dynamic coupling in older adults was further tested.

With reference to FIG. 1A, shown is an example of a system 100 for monitoring and stimulating brain activity, configured in accordance with some embodiments. In various embodiments, system 100 may be implemented for providing closed loop or open loop control in treatments and cognitive enhancements. In some embodiments, system 100 includes an interface, such as interface 102. In various embodiments, interface 102 is a brain interface that is configured to be coupled with a brain, such as brain 101. As will be discussed in greater detail below, such coupling may provide bidirectional communication, or may be used for various sensing modalities. In some embodiments, interface 102 includes various electrodes, as may be included in an electrode array. Such electrodes may be included in a scalp potential electroencephalogram (EEG) array, may be deep brain stimulation (DBS) electrodes, or may be an epidural grid of electrodes. In other examples, interface 102 may include optogenetics mechanisms for monitoring various neuronal processes. Mechanisms may be used to make various measurements and acquire measurement signals corresponding to neural activity. As used herein, neural activity may refer to spiking or non-spiking activity/potentiation.

In various embodiments, such measured signals may be electrical signals derived based on neural activity that may occur in cortical tissue of a brain. Such measurements may be acquired and represented in a time domain and/or frequency domain. In this way, neural activity may be monitored and measured over one or more temporal windows, and such measurements may be stored and utilized by system 100. In various embodiments, such neural activity may be observed for particular regions of cortical tissue may be determined, at least in part, based on a configuration of interface 102. In one example, this may be determined based on a configuration and location of electrodes included in interface 102 and coupled with the brain.

Figure 1B:
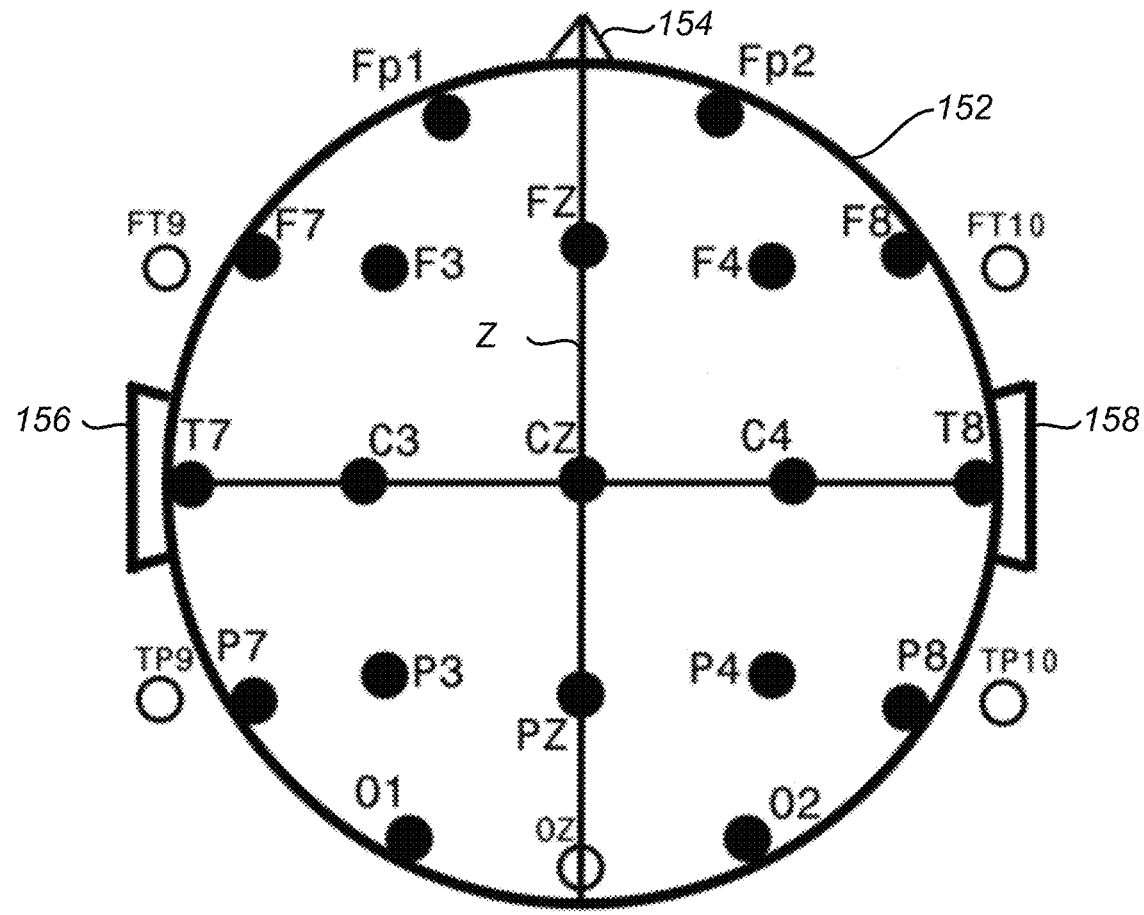
FIG. 1B illustrates an example of standard electroencephalogram electrode array which may be implemented with various embodiments.

FIG. 1B illustrates an example of standard electroencephalogram (EEG) electrode array 150 which may be implemented with various embodiments. FIG. 1B depicts standard EEG electrode names and positions along the head 152 of a user in vertex view with nose 154 above, left ear 156 to left, and right ear 158 to right. In various embodiments, EEG array 150 may be implemented as interface 102.

In various embodiments, EEG array 150 includes any number of electrodes. Such electrodes may include midline electrodes on midline Z, including FZ, Midline Frontal; CZ, Midline Central; PZ, Midline Parietal; OZ, Midline Occipital. In various embodiments, even numbers refer to right hemisphere locations, and odd numbers refer to left hemisphere locations including: Fp, Frontopolar (Fp1 and Fp2); F, Frontal (F3, F4, F7, F8); C, Central (C3, C4); T, Temporal (T7, T8); P, Parietal (P3, P4, P7, P8); O, Occipital (O1, O2). The standard 19, 10 to 20 electrodes are shown as black points. An additional subset of five, 10-10 electrodes are shown as open circles including FT, Frontotemporal (FT9, FT10); TP, Temporoparietal (TP9, TP10), and OZ. In various embodiments, EEG array 150 may include fewer or additional electrodes than shown in FIG. 1B.

According to some embodiments, one or more components of interface 102 are configured to provide stimuli to the brain coupled with interface 102. For example, one or more electrodes included in interface 102 may be configured to provide electrical stimuli to cortical tissue of the brain. As discussed above, such electrodes may be implemented utilizing one or more of various modalities which may be placed on a user's scalp, or implanted in the user's brain.

As will be discussed in greater detail below, such actuation and stimuli provided by interface 102 may be of many different modalities. For example, stimuli may be aural, visual, and/or tactile as well as being electrical and/or magnetic, or any suitable combination of these. Accordingly, interface 102 may further include additional components, such as speakers, lights, display screens, and mechanical actuators that are configured to provide one or more of aural, visual, and/or tactile stimuli to a user. In this way, any suitable combination of different modalities may be used. For example, a combination of electrical and aural stimuli may be provided via interface 102. Further still, interface 102 may include different portions corresponding to signal acquisition and stimuli administration. For example, a first portion of interface 102 may include electrodes configured to measure neural activity, while a second portion of interface 102 includes speakers configured to generate aural stimuli. In various embodiments, the visual and/or auditory stimuli may be provided via one or more communications channels that are configured to provide such stimuli. For example, such stimuli may be provided via a streaming media service or a social networking service. In one example, such stimuli may be provided via a dedicated YouTube channel that is streamed to interface 102.

In some embodiments, interface 102 further includes one or more dedicated processors and an associated memory configured to obtain and store the measurements acquired at interface 102. In this way, such measurements may be stored and made available to other system components which may be communicatively coupled with interface 102.

System 100 further includes one or more processing devices. A first processing device 104 may be configured to generate brain state parameters that may characterize and identify features of brain states and generate estimations of brain state signatures. In various embodiments, a brain state may refer to one or more identified patterns of neural activity. Accordingly, such brain states may be one or more identified patterns, such as oscillation or fluctuation of activity at a particular frequency band, such as low oscillatory behavior as well as delta, theta, alpha, beta, and gamma waves. Furthermore, such brain states may be identified based on coupling between patterns of neural activity. For example, a brain state may be identified based on oscillation or fluctuation of activity at a particular frequency band, and an increase of activity in another. Other brain states may correspond to phase resets in prefrontal and cingulate areas. Phase resets may correspond to coherent activity in widespread cortical regions and impact timing of neuronal activity. Activity patterns in the prefrontal cortex can be monitored, identified, and controlled for associations with particular behaviors including goal directed behavior. Neuronal synchronization and desynchronization may be detected and managed using closed loop control based on intelligent and continuously adaptive neurological models. As will be discussed in greater detail below, such identification may be implemented based, at least in part, on various parameters, such as observers and estimators.

Accordingly, first processing device 104 is configured to generate one or more particular observers and/or estimators that may form the basis of identification and estimation of brain states, described in greater detail below. As discussed above, first processing device 104 may be configured to generate deterministic and stochastic observers and estimators of brain states based on acquired measurements. Such deterministic observers may provide robustness to exogenous disturbances, while such stochastic estimators may provide robustness regarding noise. For example, first processing device 104 may be configured to implement linear and nonlinear observation and estimation modalities such as luenberger, kalman, sliding mode, and benes filters. The application of such observation and estimation modalities may be used to generate and infer one or more parameters associated with brain states. For example, such parameters may identify aspects of particular brain states, such as an oscillation or resonance frequency as well as a coupling and/or weighting factor associated with one or more other brain states. In a specific example, a condition of Schizophrenia may be modeled as a pair of oscillators, each being an oscillating neural pattern, and first processing device 104 may be configured to identify and determine resonance frequencies and coupling factors associated with the oscillators based on the previously described acquired measurements.

Thus, according to various embodiments, first processing device 104 may be configured to implement direct and indirect state signature estimation. First processing device 104 may also be configured to implement brain system model parameter identification and adaptation. Furthermore, first processing device 104 may also be configured to generate an estimation of the stability of underlying hidden states, as well as noise estimation and rejection in underlying measurements. In various embodiments, first processing device 104 may also be configured to implement cognitive relevance based measurement window sizing. Accordingly, measurement windows may be sized based on cognitive relevance measures, and may be sized dynamically.

In some embodiments, first processing device 104 is configured to implement baseline estimation and removal which may enhance sensitivity regarding signatures/events. As discussed above, neural activity may be measured and represented in a time domain and/or a frequency domain. In one example, when represented in a frequency domain, the neural activity may be represented as a power spectrum that follows a plot that is logarithmic or non-linear. Accordingly, in various embodiments, first processing device 104 is configured to implement one or more curve-fitting modalities to estimate a baseline of the plot, and remove such baseline to provide a more accurate representation of more granular features of the measured signal. Such granular features may be represented with greater accuracy, and be used to identify parameters of brain states with greater accuracy.

First processing device 104 may also be configured to implement learning estimator models that learn state changes and estimate them. Such learning estimator models may also learn changing system parameters, and estimate the improvement/retrograde of behavioral/functional responses.

As similarly discussed above, observers and estimators may be used to identify and/or infer state signatures and parameters associated with brain states. For example, examples of brain state signatures may include certain lower frequency oscillations mediated with or coupled to higher frequency oscillations (delta to alpha, alpha to gamma, theta to mu, alpha to high frequency band) that correspond with various levels of cognitive ability and various types of cognitive conditions to detect and identify signatures indicative of particular types of cognitive performance or cognitive conditions.

According to various embodiments, slow wave coupled spindle synchrony during sleep may be used as a signature of memory retention and consolidation. In particular embodiments, a closed loop control system may be configured to monitor and improve slow wave coupled spindle synchrony. In another example, first processing device 104 is configured to detect multiplexed parallel delta to theta, alpha to beta, delta/theta/alpha to high-frequency-band coupling to identify a signature of working memory. In yet another example, first processing device 104 is configured to monitor and/or control a baseline rate of exponential decay in a spectral composition of neural activity, as well as deviations from the baseline to identify and predict a cognitive and arousal state, such as an inhibitory or excitatory state. In various embodiments, first processing device 104 may also be configured to monitor beta synchronization or desynchronization to identify a signature of motor activity intent. In this way, any number of brain states and associated signature and parameters may be identified and estimated by first processing device 104. In some embodiments, first processing device 104 may be configured to identify an "activity silent" mode associated with a user in which a measure of activity is measured and tracked as a mental state shift indicator.

System 100 may further include second processing device 106 which is configured to generate functional and structural models of the brain coupled with interface 102. In various embodiments, second processing device 106 is further configured to provide brain functional model identification and adaptive learning, as well as brain structural models with adaptive learning. In various embodiments, second processing device 106 is communicatively coupled with interface 102, first processing device 104, as well as controller 108 discussed in greater detail below. Accordingly, second processing device 106 may receive input signals from one or more other system components and utilize such inputs to form and/or update functional and structural models of the brain coupled with interface 102. In various embodiments, second processing device 106 may also be configured to pre-process inputs received from interface 102 and first processing device 104 to generate one or more composite inputs.

In various embodiments, second processing device 106 is configured to generate functional input-output univariate and multivariate models that may be configured to approximate at least some of the input-output behavior of the brain coupled with interface 102 described above. In some embodiments, second processing device 106 is also configured to implement adaptive learning brain models that may iteratively update and improve the functional model of the brain that has been constructed.

In some embodiments, second processing device 106 is configured to implement deep/machine learning and data mining based system models. Accordingly, second processing device 106 may be configured to implement one or more artificial neural networks that may be configured to model tasks or cognitive functions of the brain. Such neural networks may be implemented in a hierarchical manner. Moreover, such neural networks may be trained based on signals received from other components of system 100. For example, models may be trained based on inputs provided to interface 102 from controller 108 and outputs measured via interface 102 as well as observers and estimators generated by first processing device 104.

In this way, input and output activity within system 100 may be used, at least in part, to construct functional and structural models represented by second processing device 106. More specifically, the artificial neural networks created by second processing device 106 may be modified and configured based on activity of the human brain. In this way, the artificial neural networks created by second processing device 106 may be specifically configured based on behaviors and processing patterns of the human mind.

In some embodiments, second processing device 106 is further configured to construct artificial neural networks that alter one or more parameters of treatment or administration of brain stimulation on an individual, based on one or more received inputs. In some embodiments, such parameters of treatment may include the schedule or nature for administration of brain stimulation treatment, as well as the time frame, duration, frequency, and/or strength of treatment following a brain injury. In some embodiments, the one or more received inputs may be received information regarding the efficacy or likelihood of success or mitigation of symptoms of a brain injury in relation to the time frame of administration of brain stimulation treatment. In some embodiments, the artificial neural networks are modified or adjusted based on updated datasets or additional input information corresponding to the timing of treatments and the results of treatments. For example, such input information may be training data that is utilized by neural networks upon which one or more machine learning algorithms are executed, such that the neural networks learn improved techniques for how to more effectively administer brain stimulation treatments, including adjusted timing, duration, frequency, and/or nature of treatments.

In various embodiments, second processing device 106 is further configured to implement system identification, dimensional modeling, and dimension reduction to identifying preferred models. Furthermore, second processing device 106 may be configured to implement identification of one or more brain states to be controlled, as may be determined based on actuation sensitivity and efficacy. In various embodiments, second processing device 106 is configured to implement identification of the most sensitive brain states to be measured. Such identification may identify the most sensitive and granular measurement that identifies the brain state changes. In some embodiments, second processing device 106 is configured to implement multi-input, multi-output measurement and actuation. In some embodiments, second processing device 106 is further configured to multi-time scale modelling (to capture the slow system and fast system dynamic accurately). In various embodiments, second processing device 106 is also configured to implement one or more neural net basis functions that may be configured and or generated based on activity of the brain. For example, such functions may include spike functions, multi-input-coevolution triggered firing (such as coherence, synchrony, coupling, correlation of two waveforms triggering a cell firing).

In some embodiments, second processing device 106 is further configured to capture or record results of treatments and various parameters and information related to treatments, including pieces of information relating to the efficacy of treatments and/or the mitigation or lack of mitigation of one or more symptoms of an injury. In some embodiments, second processing device 106 is also configured to capture or record the time frames of various treatments of individuals. In some embodiments, time frames include the timing, duration, frequency, and/or nature of treatments following the event of an injury to the brain. In some embodiments, second processing device 106 is configured to retrieve existing or historical information or datasets relating to treatments, such as information relating to the efficacy of treatments or time frame of treatments, including timing, duration, frequency, and or nature of treatments following the event of an injury to the brain.

While first processing device 104 and second processing device 106 have been described separately, in various embodiments, both first processing device 104 and second processing device 106 are implemented in a single processing device. Accordingly, a single processing device may be specifically configured to implement first processing device 104 and second processing device 106.

System 100 further includes controller 108 configured to implement and control closed loop control of treatments and cognitive enhancements. In various embodiments, controller 108 is communicatively coupled with interface 102, first processing device 104, and second processing device 106. Accordingly, controller 108 is configured to receive inputs from various other system components, and generate outputs based, at least in part on such inputs. As will be discussed in greater detail below, such outputs may be used to provide actuations to the brain coupled with interface 102. For example, outputs generated by controller 108 may be used to stimulate the brain via one or more components of interface 102. In this way, controller 108 may provide stimuli to the brain via interface 102, may receive measurements, parameter information, and model information via other components such as first processing device 104 and second processing device 106, and may generate updated stimuli based on such received information.

For example, outputs generated by controller 108 may be used to apply various stimuli via interface 102 to increase the strength or frequency of slow wave oscillations during NREM sleep in order to restore or generate phase coupling between slow wave oscillations and sleep spindles to enhance sleep-dependent hippocampus-dependent memory consolidation.

Thus, according to some embodiments, controller 108 is configured to implement multi-input, multi-output feedback control. Controller 108 may also be configured to implement loop shaping optimized feedback control. In a specific example, controller 108 is configured to implement model reference adaptive control. Furthermore, controller 108 may be configured to implement cognitive enhancement trajectory control. In various embodiments, controller 108 is configured to implement enhanced control in which one or more parameters of a treatment may be enhanced by increasing its efficiency and/or effect. For example, an input or stimulation may be reduced to implement a same enhancement, a duration of stimulations may be reduced but still reach desired improvement, and a path of recovery may be made more efficient. In this way, an amount of stimulation, which may be a combination of amplitude and duration, may be reduced while still obtaining a desired effect, thus increasing the efficacy of the treatment and reducing overstimulation. In various embodiments, controller 108 is configured to implement a genetic algorithm to identify a particular stimulation pathway that reduces an amount of stimulation.

In some embodiments, controller 108 is configured to implement combined control of pharmacological and stimulation inputs. Accordingly, controller 108 may be configured to modify stimulation inputs based on an expected effect of one or more pharmacological agents that may be administered in conjunction with the stimulation. In this way, controller 108 may modify and control administration of stimuli via interface 102 based on an identified pharmacological regimen. In various embodiments, controller 108 is configured to implement game theoretic strategy-based treatments. In some embodiments, controller 108 is configured to implement real time measurement/estimation and control.

In various embodiments, controller 108 is configured to receive a reference signal which may be used, at least in part, to generate or modify the stimuli provided via interface 102. In various embodiments, the reference signal may be a previously determined signal or pattern that may represent a reference level or pattern of neural activity. In some embodiments, the reference signal may be generated based on a "negative" model. In a specific example, such a negative model may be a functional and/or structural model that is generated based on a reverse or inversion of one or more of the models created and stored by second processing device 106. Accordingly, such a negative model may be generated by second processing device 106, and the reference signal may be generated by second processing device 106 and received at controller 108.

As will be discussed in greater detail below, the above-described components of system 100 may be specifically configured to provide one or more particular applications. For example, system 100 may be configured to provide bio-signal interpretation for status monitoring and diagnostics. Accordingly, the brain state information observed and derived by at least first processing device 104 and second processing device 106 may be used to identify brain states, the onset of particular brain states, and particular transitions between brain states. Such events may be detected, and notifications may be generated by, for example, first processing device 104, second processing device 106, or controller 108. Such notifications may be provided to other entities, or client devices 110, that may be involved in status monitoring and diagnostics, such as computing and mobile devices associated with medical professionals, or a user's in-home medical system.

In various implementations, client device 110 may be any one of various computing devices such as laptop or desktop computers, smartphones, personal digital assistants, portable media players, tablet computers, or other appropriate computing devices that can be used to communicate over a global or local network, such as the Internet. In various embodiments, client device 110 may be configured to communicate with the first processing device 104, second processing device 106, and/or controller 108.

In some embodiments, client device 110 may receive information from the various other components, such as device status, performance or function information, predictive models, brain state parameters, diagnostic information, mediation procedures, etc. For example, the brain state parameters generated by first processing device 104 may be transmitted to client device 110. In some embodiments, functional and structural models of the brain generated by second processing device 106 may be transmitted to client device. As another example, particular control signals may be communicated to controller 108 from client device 110 to be sent to interface 102 or prosthetic 112. In some embodiments, client device 110 may also be configured to directly communicate with interface 102 or prosthetic 112, for example to transmit control signals or monitor device status.

Moreover, system 100 may be configured to provide augmented reality (AR)-virtual reality (VR) for cognitive enhancements and side-effect removal. For example, brain state and associated parameter detection may be used to identify the onset of particular cognitive states, such as motion sickness. When detected, or even when the onset is detected, controller 108 may generate one or more stimuli, which may be visual stimuli, tactile stimuli, and/or electric stimuli, to alleviate the detected cognitive state. In this way, motion sickness associated with VR may be alleviated. In various embodiments, brain stimulation may be used to enhance sensory perception associated with AR and VR. Accordingly, one or more stimuli may be provided via interface 102 where such stimuli are determined based on the AR or VR program, and such stimuli may enhance or improve the experience of the AR or VR program.

In various embodiments, system 100 is configured to provide cognitive and behavioral modulation specific to a particular psychological or neurophysiological condition. For example, a condition such as depression may be characterized by a frozen brain state, or a brain state that does not oscillate as a normal brain would. In various embodiments, system 100 may be configured to identify a particular brain state, identify that it is "frozen" (has not changed over a designated period of time), and generate one or more control signals that are configured to stimulate the user's brain and change the brain state of the user by virtue of the stimulation to alleviate the depression. In another example, such generation of control signals may be used to alleviate or manage pain, as may be applicable with chronic pain. Such control signals associated with pain management may be implemented using multi-modal (multi-sensory) stimulation. In yet another example, generation of control signals may be utilized for stimulation based reversal of 'minimally-conscious' or 'comatose' brain states of users. In an additional example, such control signals may be used to mitigate or alleviate age based cognitive decline. Accordingly, stimuli may be provided via interface 102 to stimulate areas having diminished activity due to the process of aging.

In some embodiments, system 100 may be configured to provide system and pathology specific functional brain models, as may be utilized in pharmacological applications. Accordingly, as discussed above, the use of pharmacological agents may be identified, and models may be updated in response to such pharmacological agents being identified. In this way, administration of stimuli via interface 102 may be modified and updated based on the application of a pharmacological agent to a user. More specifically, such modifications may be implemented based on the identification of the use of pharmacological agents, as well as directly measured neural activity of the user during the treatment process.

In another example, system 100 may be configured to provide model based adaptive control paradigms for feedback treatments and cognitive enhancements. Accordingly, as discussed above, treatments and cognitive enhancements may be provided with adaptive closed loop control that enables the modification and updating of such treatments and cognitive enhancements based on directly measured neural activity over the course of the treatments and cognitive enhancements.

In various embodiments, system 100 may be configured to provide smart embedded prosthetics (e.g. speech decoder, motor control). Accordingly, signals generated by controller 108 may be used to control one or more embedded prosthetics, such as prosthetic 112. In some embodiments, prosthetic 112 may be an implanted stimulator that may be activated by controller 108 in response to the detection or identification of one or more brain states or parameters associated with such brain states. In some embodiments, prosthetic 112 may be a component of interface 102 or communicatively coupled to interface 102.

In a specific example, prosthetic 112 may be a stimulator configured to increase the strength or frequency of slow wave oscillations in the medial prefrontal cortex (mPFC). In another example, prosthetic 112 may be a stimulator configured to prevent epileptic episodes. In this example, controller 108 may identify a brain state corresponding to an onset of an epileptic seizure, and may provide a signal to prosthetic 112 that activates prosthetic 112 to prevent the seizure. For example, prosthetic 112 may comprise a multi-channel closed-loop neural-prosthetic system-on-chip (SoC) configured for real-time intracranial electroencephalogram (iEEG) acquisition, seizure detection, and electrical stimulation in order to suppress epileptic seizures.

In some embodiments, system 100 may be configured to provide a toolbox configured to support estimation, modeling, and control. In another example, system 100 may be configured to provide a bio operating system (BoS) framework for biological measurement and an actuation control platform. As discussed above, such an operating system may be implemented on a variety of platforms including a mobile platform such as mAndroid. In some embodiments, system 100 may be configured to provide task specific cognitive enhancements, such as FAA monitoring agents, and fighter pilot related tasks.

System 100 and its respective components may be implemented in a variety of contexts. For example, system 100 may be implemented in a clinical setting that may include an examination room, an operating room, or an emergency room. Moreover, system 100 may be implemented in a user's home thus providing in-home monitoring, diagnostic, and treatment. Furthermore, portions of system 100 may be implemented in a first location while other portions are implemented in a second location. For example, interface 102 may be located at a user's home, while first processing device 104, second processing device 106, and controller 108 are implemented remotely, as may be the case when implemented at a hospital.

Furthermore, system 100 may be implemented across multiple users. For example, system 100 may include multiple interfaces that are coupled with multiple brains. In this way, measurements may be made from multiple users, and stimuli may be provided to multiple users. In one example, measurements from a first user may be used to generate and provide stimuli to a second user. In this way, synchronization of at least part of a brain state may be implemented across multiple users.

Other systems, devices, and methods for monitoring and stimulating brain activity described in U.S. patent application Ser. No. 16/170,675 titled MEDIATION OF TRAUMATIC BRAIN INJURY by Pradeep et al., filed on Oct. 25, 2018, which application is incorporated by reference herein in its entirety and for all purposes.

Unique non-linear directional cross-frequency coupling (CFC) analyses were implemented, together with phase-dependent correlation measures, to capture complex neural dynamics underlying SO-spindle synchrony relationships. Based on theoretical accounts of oscillation-based timed memory transfer, the hypothesis that the exact timing between SO and spindles supports memory consolidation was tested. Building on the prediction that SO orchestrate sleep-dependent memory networks, implemented methods for assessing the temporal directionality of this SO-spindle interaction were implemented, and examined if this directionality predicted memory consolidation success in young and older adults. Finally, it was tested whether regional gray matter atrophy within the mPFC, relative to other control regions, provided a structural correlate associated with the age-related degradation of SO-spindle coupling and associated memory decline in older adults.

Figures 2A, 2B:
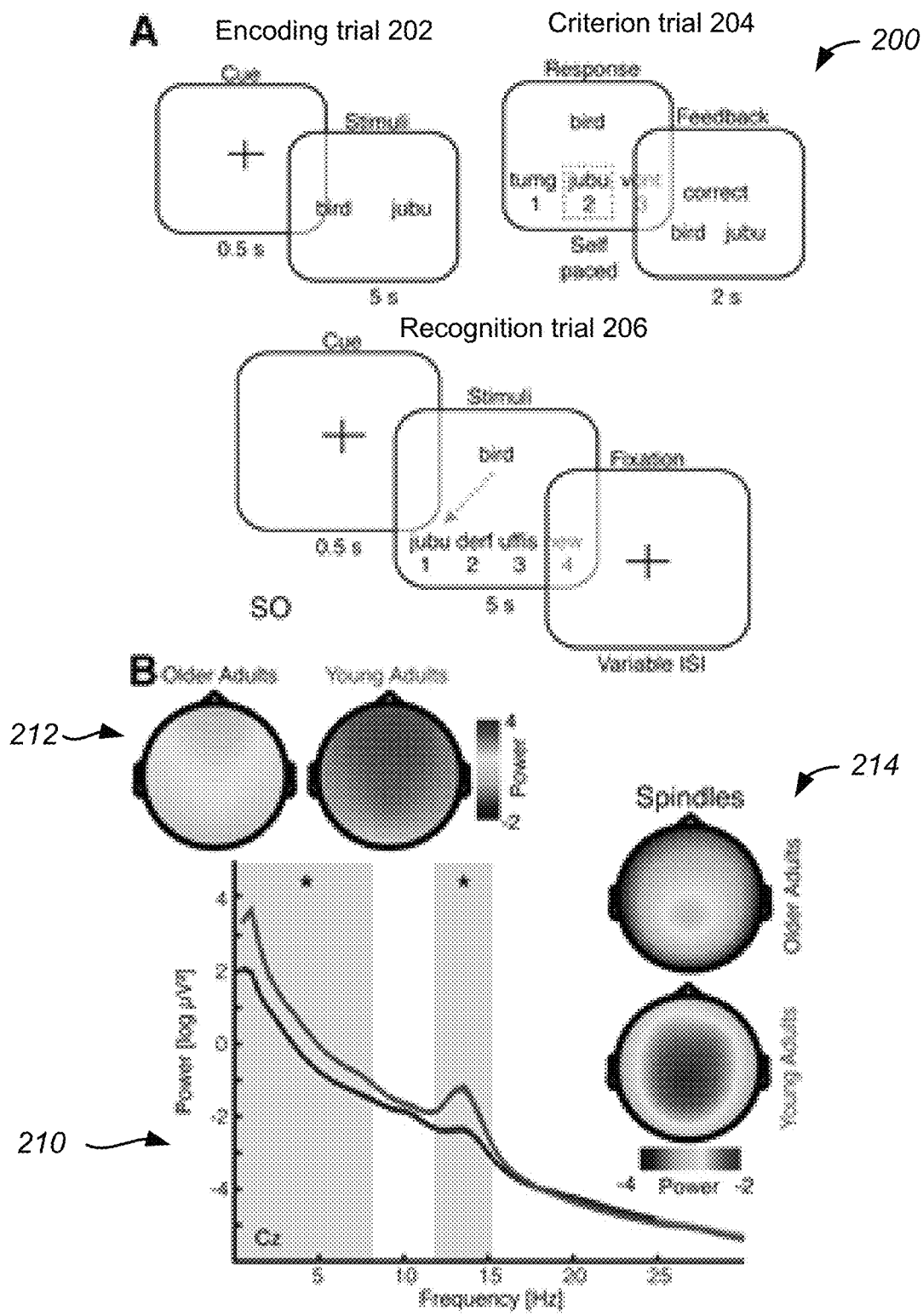
FIGS. 2A-2D illustrate memory task and oscillatory signatures of sleep, in accordance with some embodiments.

Cognitively normal older (n=32; age: 73.8±5.3; mean±SD) and young (n=20; 20.4±2.0 years) participants performed a sleep-dependent episodic memory test before and after a full night of sleep (FIG. 2A). After encoding, all participants were trained to 100% criterion before initial recognition testing (short delay; after ~10 min). After the short delay test, participants underwent polysomnography in the lab and were given an 8 h sleep period starting at their habitual bedtime. They performed the second recognition test (long delay; after ~10 h) the next morning. Then structural MRI data to assess gray matter (GM) intensity were obtained. Memory retention was quantified as the difference between recognition performance at the long delay minus performance at the short delay. Consistent with existing, overnight memory retention was impaired in older adults relative to young adults ($t_{46}$=−3.85, p=0.0004, d=1.19), leading to the next-step quantification of differences in NREM oscillatory dynamics that may underlie these age-associated memory impairments.

Oscillatory Dynamics of Sleep in Old and Young Adults:

EEG power differences between older and young adults were first assessed by means of cluster-based permutation tests across all frequencies and channels during NREM sleep (FIG. 2B; with all figures displaying data from electrode Cz due to the spatial distribution of SO and spindle power, unless stated otherwise). Oscillatory power was significantly lower in older adults from 0.5 to 8.5 Hz (p=0.0020, d=1.71) as well as between 10.5 and 15 Hz (p=0.0080, d=1.28) in all recorded channels (FIG. 2B).

Next, SO (0.16-1.25 Hz) and sleep spindle (12-16 Hz) events were detected based on established algorithms. Analysis of inter-spindle intervals indicated that sleep spindles exhibited a non-Poisson like behavior and were preferentially separated by 1.13-2.78 second (s) during NREM sleep, which is in accordance with the idea that <1 Hz SO controls sleep spindle timing and separates them by at least 1-3 cycles.

Figures 2C, 2D:
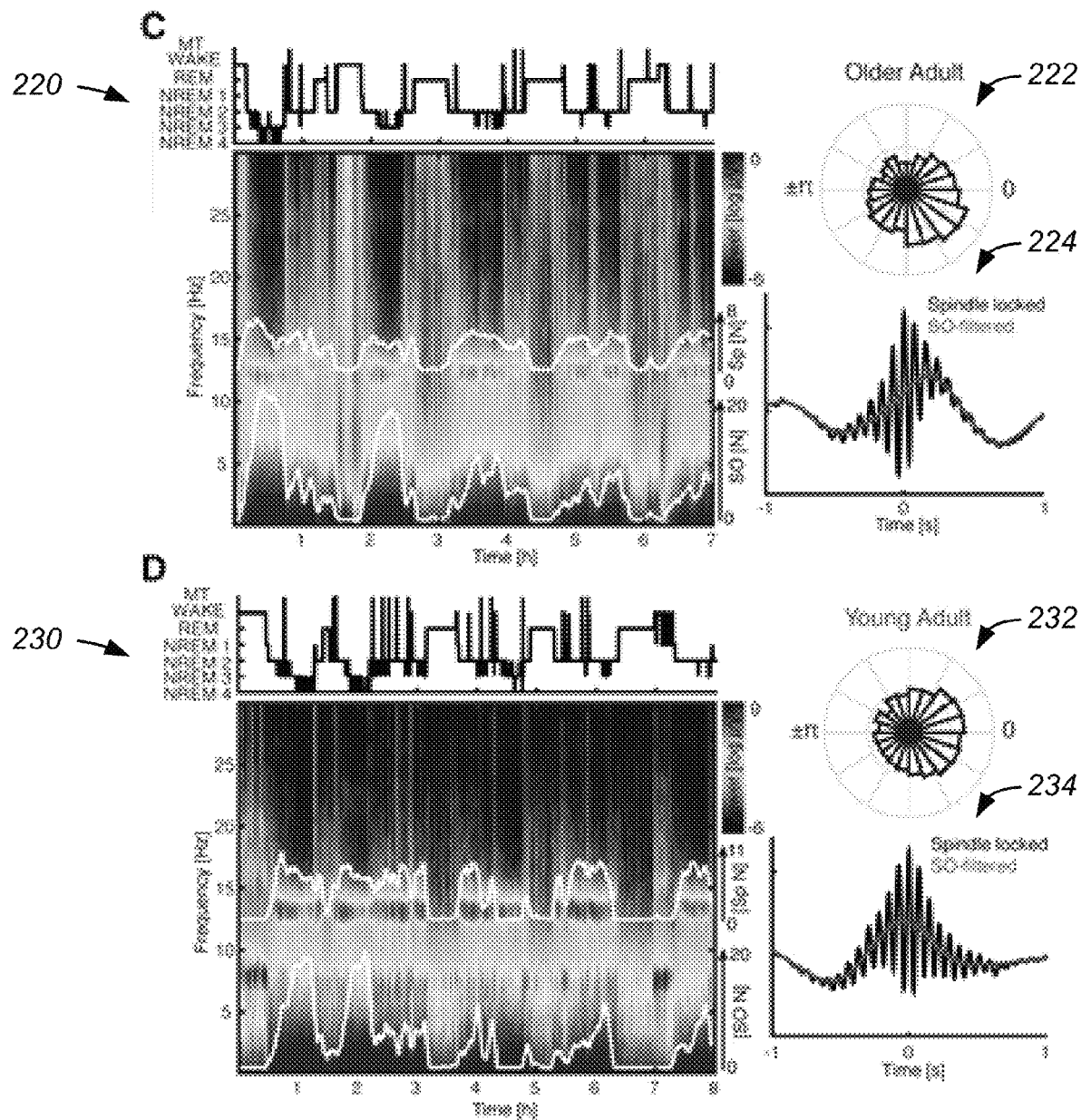
Figures 3A, 3B, 3C, 3D:
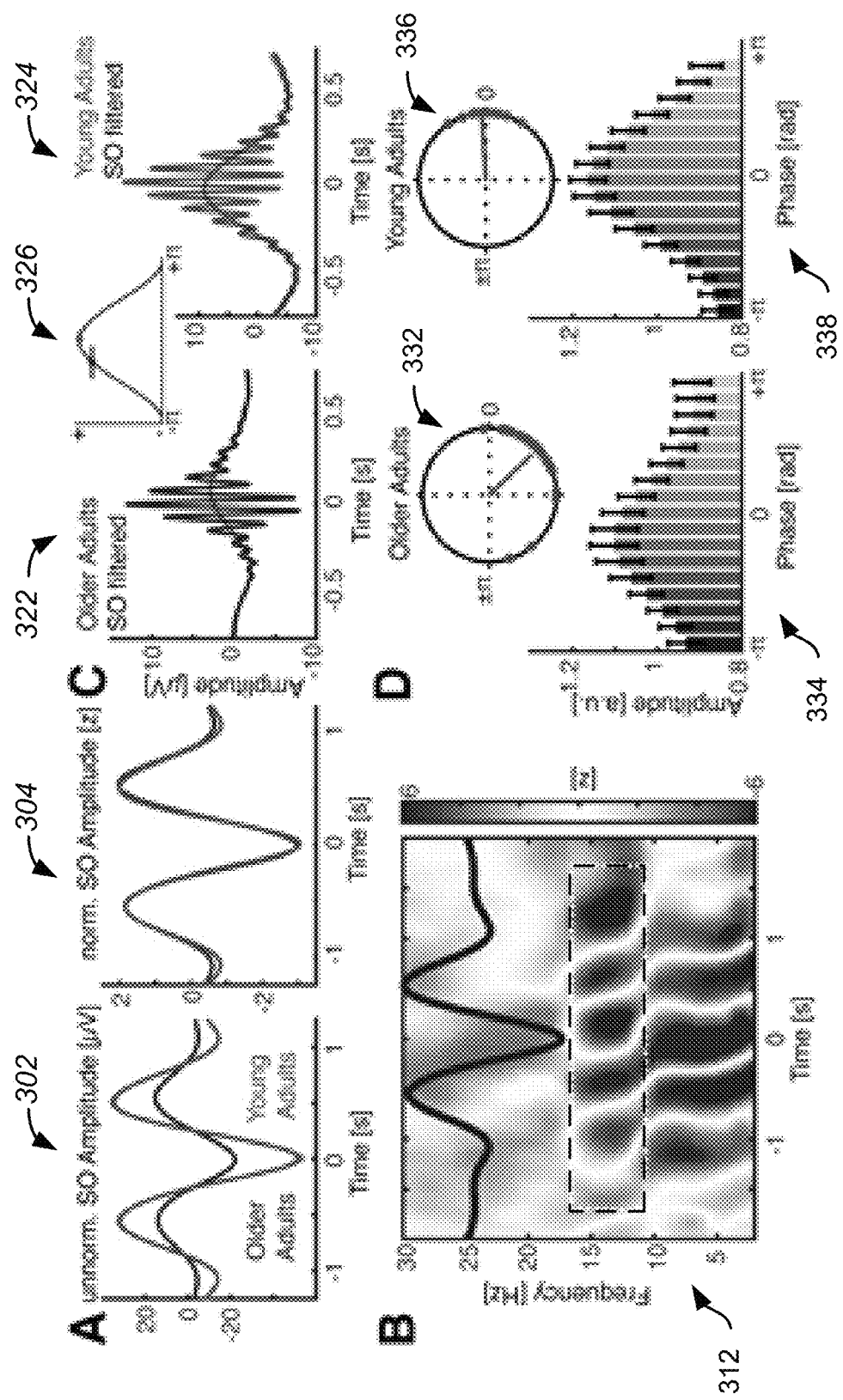
FIGS. 3A-3G illustrate SO-Spindle interactions in old and young adults, in accordance with some embodiments.

Detection of SO and sleep spindle events reliably tracked spectral sleep signatures over a full night of sleep (FIGS. 2C and 2D for exemplary old/young subjects; numbers of detected events are superimposed in white). For every participant, the SO phase during the peak of the detected sleep spindle events was determined. Significant non-uniform circular distributions were identified in 29/32 old adults and in 20/20 young adults. Of note, differences in oscillatory power can distort cross-frequency coupling estimates. This issue was addressed by z-normalizing individual events in the time domain to alleviate amplitude differences prior to all subsequent analyses (FIG. 3A). Note that this normalization avoids spurious coupling that has been recently pointed out as a potential confound in cross frequency analysis. To further address this concern, a validated stratification approach was also employed, confirming the main findings.

Additional details are now provided regarding FIGS. 2A-2D which relate to memory task and oscillatory signatures of sleep. FIG. 2A illustrates episodic word-pair task 200. Participants learned 120 word-nonsense word pairs. Nonsense words were 6-14 letters in length, derived from groups of common phonemes. During encoding trials 202 (upper left) word pairs were presented for 5 s. Participants completed the criterion training 204 (upper right) directly after encoding and received feedback after every trial. Recognition trials 206 (lower panel) were performed after a short delay (10 min, 45 trials) and again after a full night of sleep (10 h, 135 trials). FIG. 2B illustrates EEG power spectra 210 during NREM sleep at electrode Cz for older (blue) and young (red) adults (mean±SEM). Grey shaded areas indicate significant differences in low and sleep spindle frequency ranges. Inset 212 depicts topographical distribution of SO (<1.5 Hz; upper topographies) and inset 214 depicts sleep spindle (12-16 Hz; topographies on the right) power. Note that older subjects exhibited significantly reduced oscillatory power across the whole head. Regarding FIG. 2C, in the upper left: Hypnogram 220 (MT=movement time) from one exemplary of older subject and full night multi-taper spectrogram at Pz (lower left) with superimposed number of detected SO and sleep spindle events (white solid lines; 5 min averages). Upper right: Normalized circular histogram 222 of detected spindle events relative to the SO phase for older subjects. Note the peak in the right lower quadrant. Lower right: Graph 224 shows Peak-locked sleep spindle average across all detected events in NREM sleep (black). Low-pass filtered events (red) highlight that the sleep spindles preferentially peaked prior to the SO 'up-state'. FIG. 2D illustrates an example of a young subject. Same conventions as in FIG. 2C. Upper left: Hypnogram 230 from one exemplary of young adult subject and full night multi-taper spectrogram at Pz (lower left) with superimposed number of detected SO and sleep spindle events (white solid lines; 5 min averages). Upper right: Normalized circular histogram 234 of detected spindle events relative to the SO phase for young adult subjects. Lower right: Graph 234 shows Peak-locked sleep spindle average across all detected events in NREM sleep (black). Note, that low-pass filtered events (red) highlight that the sleep spindle amplitude is increased after the SO peak.

Aging Affects Prefrontal SO-Spindle Coupling:

Following normalization, SO trough-locked time-frequency spectrograms were first calculated separately for older and young adults and then compared using a cluster-based permutation approach. Multiple significant clusters were observed in the sleep spindle range (FIG. 3B; p=0.0160, d=1.73). Interleaved patterning in the spindle range (dashed box, FIG. 3B) demonstrated that the timing of sleep spindles relative to the SO was different between older and young adults. Specifically, spectrograms illustrated that sleep spindles peaked before, rather than in time with, the SO peak in older relative to young adults (inset 326 in FIG. 3C).

Mean sleep spindle activity was nested just after the SO peak in young adults, but was misaligned in older adults, occurring earlier in the rising flank of the SO (see FIGS. 3B and 3C). Significant non-uniform distributions were present for both older (Rayleigh z=23.24, p<0.0001) and young adults (Rayleigh z=18.55, p<0.0001). However, the mean coupling direction differed significantly between groups (FIG. 3D; older adults: −46.3°±31.2'; young adults: 3.6°±15.5°; circular mean±SD; Watson-Williams test: F1, 50=41.34; p<0.0001; η2=0.44). That is, spindles in young adults were maximal just after the SO peak, while sleep spindles in older adults were misaligned, prematurely peaking earlier on the rising phase in the SO cycle. This effect was not confounded by differences in spindle onset phase angles or differences in spindle duration.

Next, differences in coupling strength between groups were assessed using two complementary analyses: 1) an event-locked coupling approach that extracted the resultant vector length per subject for all SO-spindle events at every electrode, and 2) a data-driven approach based on the modulation index and screening of a wide-range of phase-amplitude pairs.

Figures 3E, 3F, 3G:
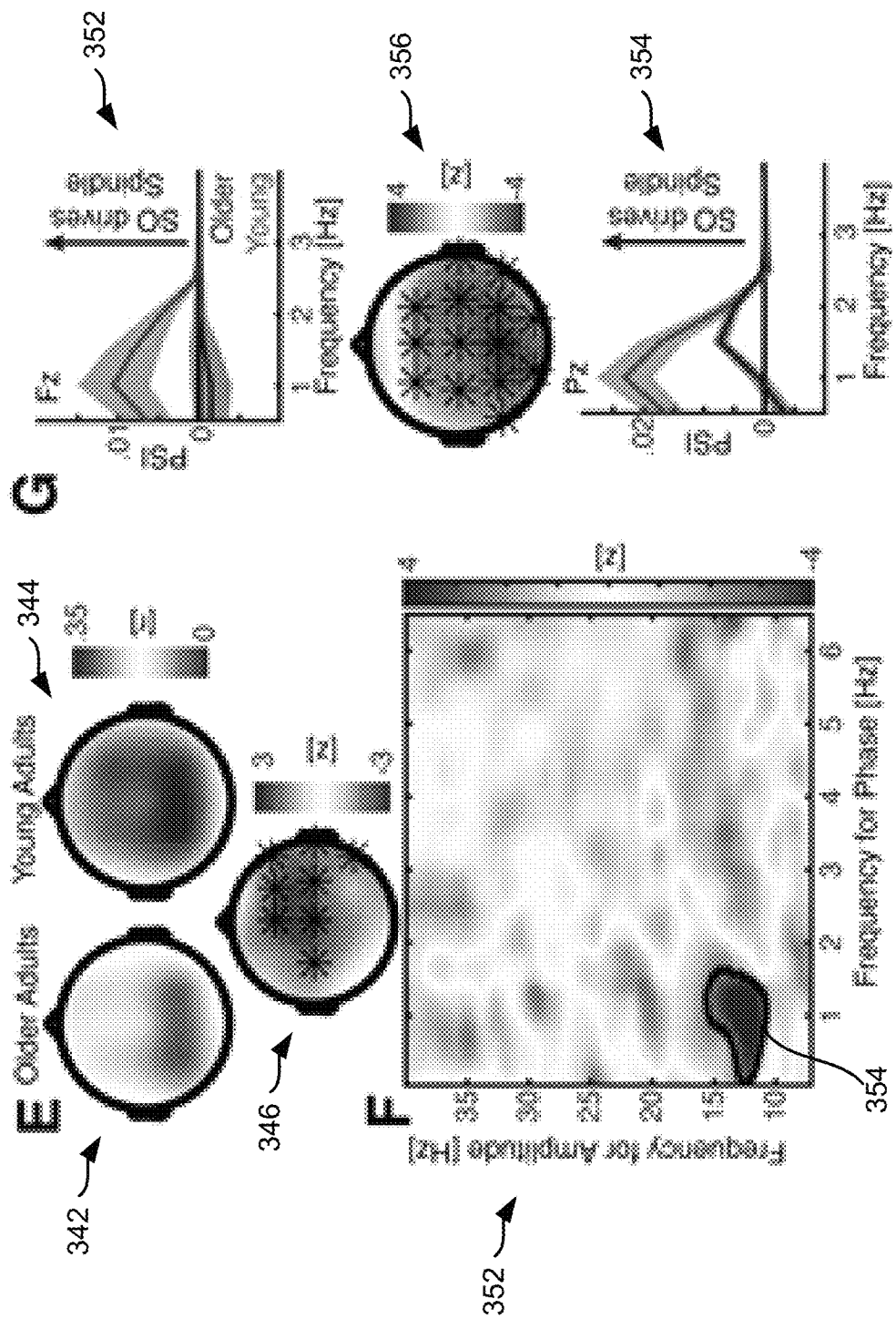

For the first analysis, significant cluster difference in frontal topography was identified for older and young adults (p=0.0120, d=0.76), indicating that SO-spindle coupling was most impaired over fronto-central sensors (FIG. 3E). The second, data-driven analysis, confirmed that this fronto-central cluster effect was specific to the SO-range between the 0.5-2 Hz and the 12-16 Hz range (p=0.0150, d=0.92), indicating that stronger coupling in young adults was limited to the SO-spindle range (FIG. 3F). Both approaches were highly correlated (rho=0.7645, p<0.0001) and effects were not simply driven by differences in the number of oscillatory events.

Cortical Slow Oscillations Coordinate Spindle Activity:

Having established differences in SO-spindle coupling between young and older adults, and building on our hypothesis and past theoretical models of SO driving spindle coordination, investigated directional influences between SO and sleep spindles by means of the phase slope index (PSI) was investigated next.

A cluster-based permutation test revealed that the directional influence of SO on sleep spindle activity was impaired in older as compared to young adults over frontal and parieto-occipital regions (FIG. 3G; p=0.0010, d=0.81). However, while parieto-occipital directional CFC was markedly reduced in older adults, it was still above zero. This demonstrates that the parietal physiologic SO-spindle coupling was partially intact in older adults.

To examine directionality, it was tested whether the PSI predicted how much time the sleep spindle deviated from the SO peak. A significant frontal cluster was identified over fronto-central sensors, indicating that larger PSI values predicted a smaller deviance—that is, a sleep spindle peak closer to the 'up-state' in young relative to older adults (p=0.012, mean rho=−0.3367; older adults: 205.07±18.68 ms; young adults: 60.24±8.26 ms; mean±SD). This PSI analysis demonstrated two findings: 1) The SO phase predicts spindle timing over frontal sensors, rather than the converse, as postulated by theoretical models that SO triggers spindle events, and 2) the timing precision was misaligned, since directional influences were reduced in older adults relative to young adults.

Additional details are now provided regarding FIGS. 3A-3G which relate to SO-Spindle interactions in old and young adults. FIG. 3A illustrates graph 302 on the left: Trough-locked SO grand average for older (blue) and young (red) adults. Note the prominent differences in amplitude. FIG. 3A also illustrates graph 304 on the right: the SO amplitude was normalized for every subject prior to all other analyses to alleviate spurious effects, which could be the result of prominent power and signal-to-noise differences. FIG. 3B illustrates a statistical map 312 of SO-locked power differences across time between older and young subjects. Note the interleaved patterning in the sleep spindle range (12-16 Hz; dashed box). As reference, the mean SO is superimposed (black line; rescaled). FIG. 3C illustrates graph 322 on the left: Peak-locked spindle grand-averages for older adults (blue) with superimposed low-pass filtered signal (black). FIG. 3C also illustrates graph 324 on the right: Peak-locked sleep spindle grand-average for young adults (red) with superimposed low-pass filtered signal (black). FIG. 3C also illustrates inset 326 at the top: Averaging mean coupling phase and SD on schematic SO (cosine).

FIG. 3D illustrates graphs 332 (older adults) and 336 (young adults) in the upper portion: The red line indicates the mean SO phase where sleep spindle power peaks. Red dots depict individual subjects. Note sleep spindle power in older adults peaks prior to the SO positive peak (0°), while sleep spindle power in young subjects peaks around 0°. FIG. 3D further illustrates graphs 334 (older adults) and 338 (young adults) indicating the grand-average normalized spindle amplitude binned relative to the SO phase. Again, note the non-uniform distribution, which peaks around 0° for young adults, but earlier for older adults.

FIG. 3E illustrates in the upper: SO-spindle coupling strength (resultant vector length) topography 342 for older adults (left) and SO-spindle coupling strength topography 344 for young adults (right). The lower portion of FIG. 3E illustrates a statistical difference map 346, which indicates that the coupling strength was significantly reduced for fronto-central EEG sensors, while parieto-occipital estimates did not differ (each star or asterisk denotes cluster-corrected two-sided p<0.05). FIG. 3F illustrates a statistical map 352 of a data-driven comodulogram. The black-circled area 354 highlights the significant difference between older and young adults, which was confined to the SO-spindle range. FIG. 3G illustrates cross-frequency directionality analyses. Values above zero indicate that SO drive sleep spindle activity. Graph 352 in the upper panel indicates that frontal SO drive sleep spindle activity in young but not older adults (electrode Fz), while graph 354 in the lower panel indicates that parieto-occipital SO predicts sleep spindle activity in both older and young adults (lower panel; Pz). However, this effect is pronounced for young adults (red). The topography 356 (center panel) depicts the spatial extent where directional SO-spindle influences are reduced in older adults relative to young adults. Note that this effect was independent of the chosen window length.

SO-Spindle Coupling Predicts Overnight Memory Consolidation:

Having characterized the oscillatory dynamics of SO-spindle coupling and identified impairments in these dynamics in older relative to young adults, the hypothesis that these oscillatory dynamics predicted overnight memory retention success, and associated age-related differences, was tested. Note that traditional linear correlation analyses were not applicable given that phase is a circular metric. Cluster-corrected circular-linear correlation analyses were used to assess the non-linear relationship between optimal coupling phase and behavior.

Figures 4A, 4B:
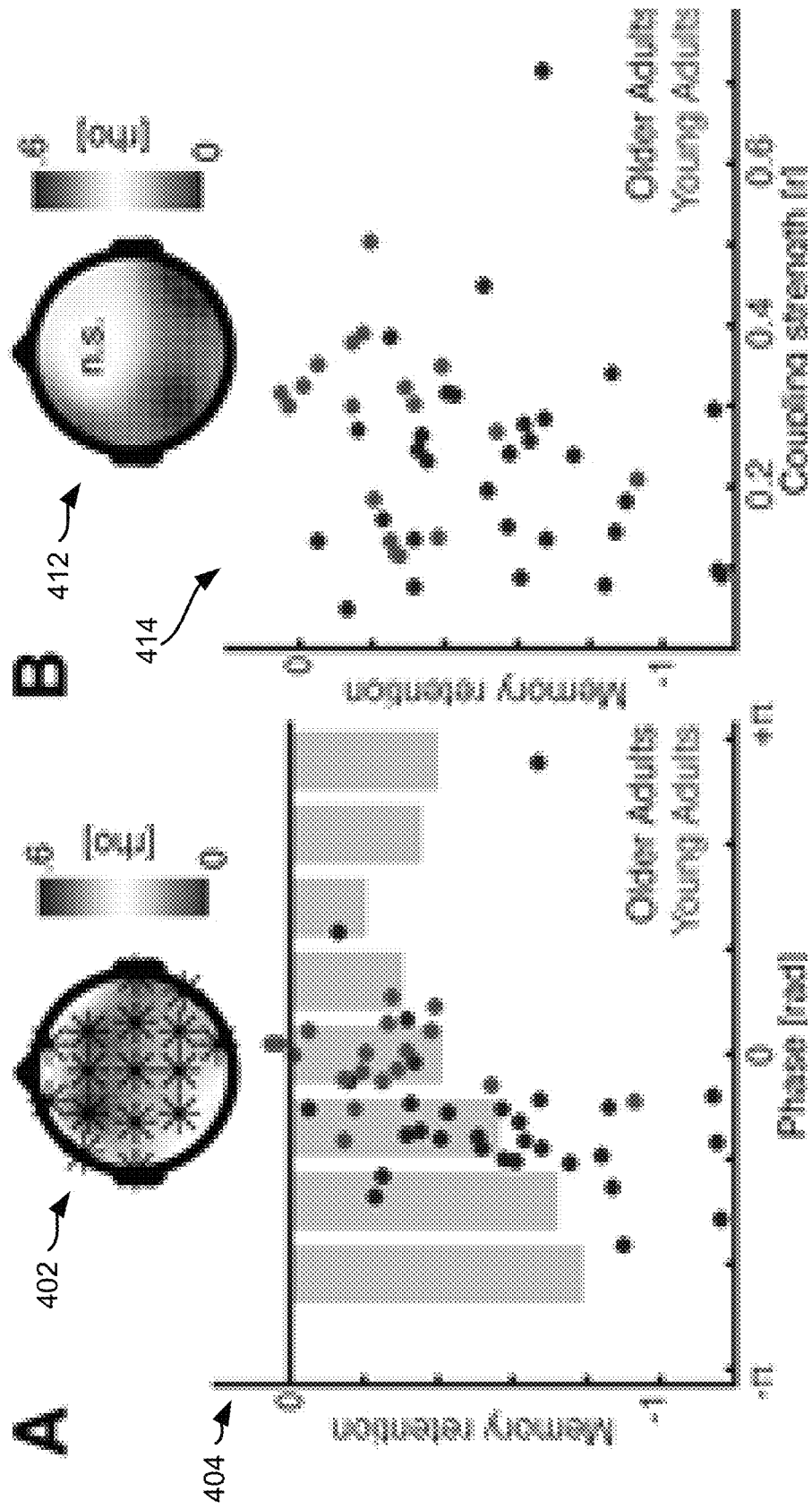
FIGS. 4A-4D illustrate timing of SO-spindle interactions predicting memory retention, in accordance with some embodiments.

A significant positive cluster was identified over frontal regions (p=0.0010, mean rho=0.4353) peaking at electrode F3 (rho=0.5699; FIG. 4A). To further delineate and visualize this non-linear relationship, the average memory retention scores were binned relative to the individual mean coupling direction (10 bins, overlap: ±1 bin; grey shaded; FIG. 4A). The resulting distribution followed an inverted u-shape, demonstrating that the success of overnight memory consolidation was achieved when the spindle event occurred most proximal to the SO 'up-state' peak. When spindles occurred further from that 'up-state' peak, the predictive influence on overnight memory retention success declined. Note this finding was not confounded by demographic or sleep architecture differences.

No other significant EEG clusters were identified when SO-spindle coupling strength was correlated with the degree of overnight memory retention across all subjects (FIG. 4B). To assure that these results were robust against differences in oscillation power and peak frequency, sleep spindle peak and amplitude distribution confounds (FIG. 4C) were corrected for by detecting the individual sleep spindle peak frequency for every SO event. A significant positive cluster was observed (p=0.0040, mean rho=0.3790), which peaked at electrode C4 (FIG. 4D, rho=0.4705) indicating that the coupling phase robustly predicted overnight memory retention.

Importantly, this effect peaked in both older and young adults at neighboring electrodes (C4 in older adults: rho=0.5725; Cz in young adults: rho=0.5678). This result demonstrates that, even though older adults showed a reduction in SO-spindle coupling, and lower overnight memory retention than young adults, the same predictive functional relationship between SO-spindle coupling and memory consolidation success was observed in both groups.

Figures 4C, 4D:
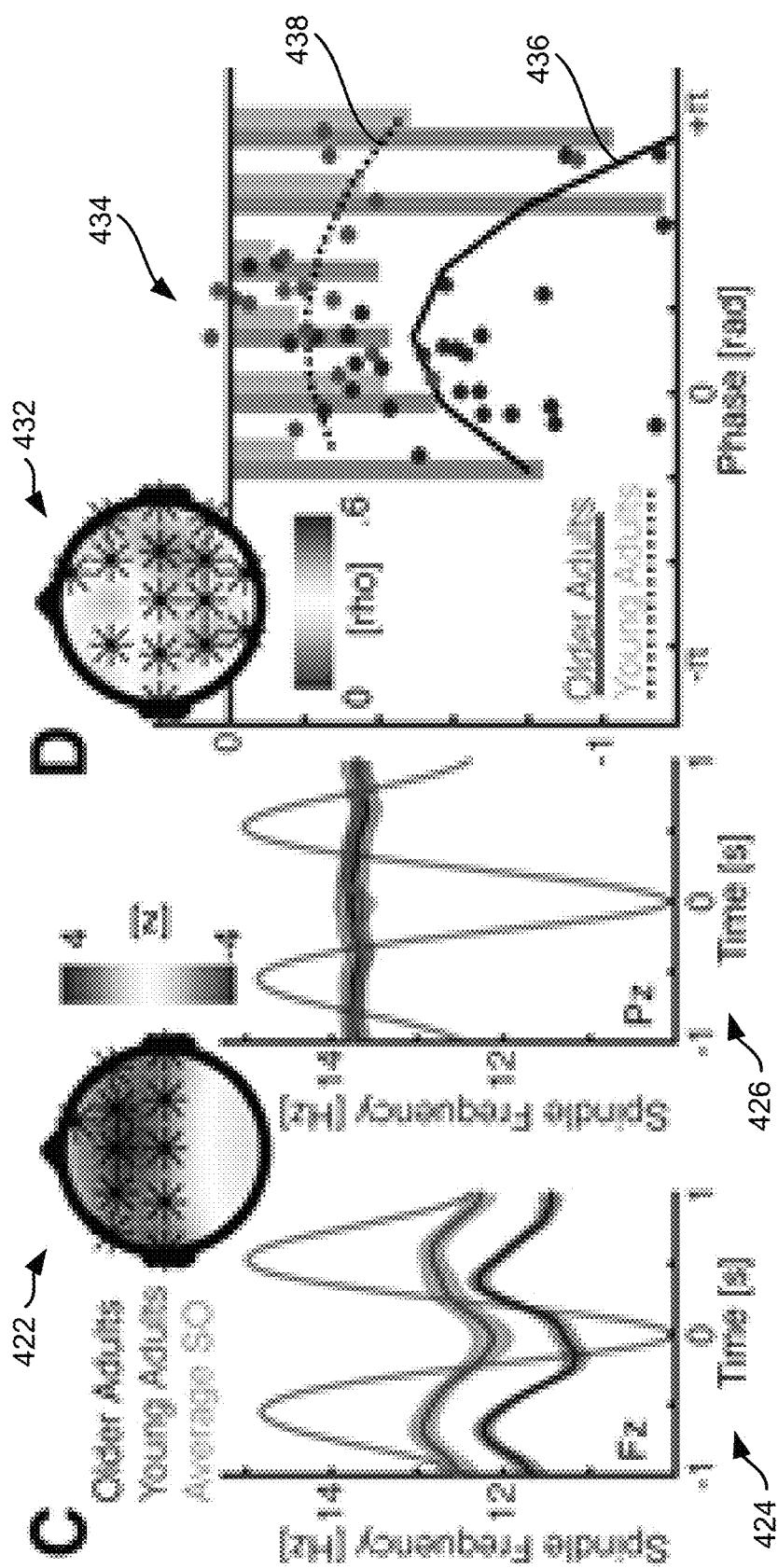

Performance for older and young adults was binned, allowing the expression of the quadratic fits to highlight the inverse u-shaped relationship indicated by the circular-linear correlations (FIG. 4D). These findings confirmed that after correcting for power and peak frequency differences, the degree of overnight memory retention success was still predicted by the timing of the coupled relationship between the SO and spindle (FIG. 4D). Therefore, memory consolidation success was most accurately predicted by sleep spindle amplitude peaking just after the SO 'up-state' peak.

Additional details are now provided regarding FIGS. 4A-4D which illustrate how the timing of SO-spindle interactions predicts memory retention. FIG. 4A illustrates topography 402 in the upper, which shows cluster-corrected circular-linear correlation analysis between the individual mean SO-spindle coupling phase and overnight memory retention after correction for power differences (* indicates significant sensors). The strongest effect was observed at electrode F3. FIG. 4A also illustrates graph 404 in which blue dots indicate older adults and red dots indicate young adults. The mean behavioral performance were binned relative to the coupling phase in 10 overlapping bins to highlight the u-shaped, non-linear relationship. FIG. 4B illustrates topography 412 and graph 414 showing no significant correlation being observed between coupling strength (resultant vector length) and memory retention (same conventions as in FIG. 4A).

FIG. 4C illustrates sleep spindle frequency relative to SO cycle at a frontal electrode (left graph 424) and at a parieto-occipital electrode (Pz) (right graph 426). Frontal sleep spindles are slower than posterior sleep spindles. Their frequency only varies as a function of the SO phase over frontal regions where it is significantly lower for older adults as shown in topography 422 (top panel). FIG. 4D illustrates topography 432 and graph 434 showing cluster-corrected circular-linear correlations after correcting for differences in power distributions and sleep spindle frequencies (same conventions as in FIG. 4A). Importantly, memory retention was coupling phase dependent in older and young adults. Overall the best performance was observed when the sleep spindles peak just after the SO peak. Blue dots depict older adults. Dark grey bars indicate mean binned memory performance for older adults; the black solid line 436 depicts a quadratic fit to approximate the non-linear u-shaped relationship for older adults. Red dots depict young adults. Light grey bars indicate mean binned memory performance for young adults; and the dashed black line 438 depicts a quadratic fit to approximate the non-linear u-shaped relationship for young adults.

Age-Related Grey Matter Atrophy Predicts Coupling Deficits:

Collectively, the above analyses established 1) the oscillatory dynamics of SO-spindle coupling, demonstrated impairments in these dynamics in older relative to young adults, and 2) identified that the spatiotemporal precision of SO-spindle coupling predicted the degree of overnight memory retention success and when impaired in older adults, predicted greater overnight forgetting.

Finally, the study sought to determine a potential underlying pathological mechanism accounting for why older adults suffer these impairments. The study focused a priori on mPFC grey matter, based on the prominent role of the mPFC in SO oscillatory generation. Specifically, the hypothesis that mPFC grey matter atrophy predicts the degree of compromised SO-spindle dynamic coupling was tested.

To rule out age-related confounds, all structural metrics by the total intracranial volume were corrected, which were correlated (rho=−0.2919, p=0.0358). cluster-based permutation correlation analyses was then utilized to assess whether the grey matter volume in any ROI predicted directional SO-spindle coupling as measured by the PSI. Consistent with the hypothesis, grey matter volume in mPFC positively correlated with directional coupling (FIG. 5A; p=0.0080, mean rho=0.3321), indicating that as grey matter volume in mPFC decreases, directional phase coupling between SO and sleep spindles is weakened. Note, that the results were comparable when corrected for total brain volume (r=0.29, p=0.0343). In addition, age was partialled out from the cluster-based correlation test (see Methods) and again obtained a significant frontal cluster (p=0.0490; mean rho=0.25).

While our results confirmed the key role of SO in the coupling dynamics and associated memory consolidation benefit, sleep spindles, which are grouped by the SO, are anatomically recognized to be thalamo-cortical mediated events. Given these findings additional post-hoc analyses were performed to examine whether grey matter volume in these spindle-associated regions also predicted impairments in SO-spindle coupling the associated memory benefit.

Figures 5A, 5B:
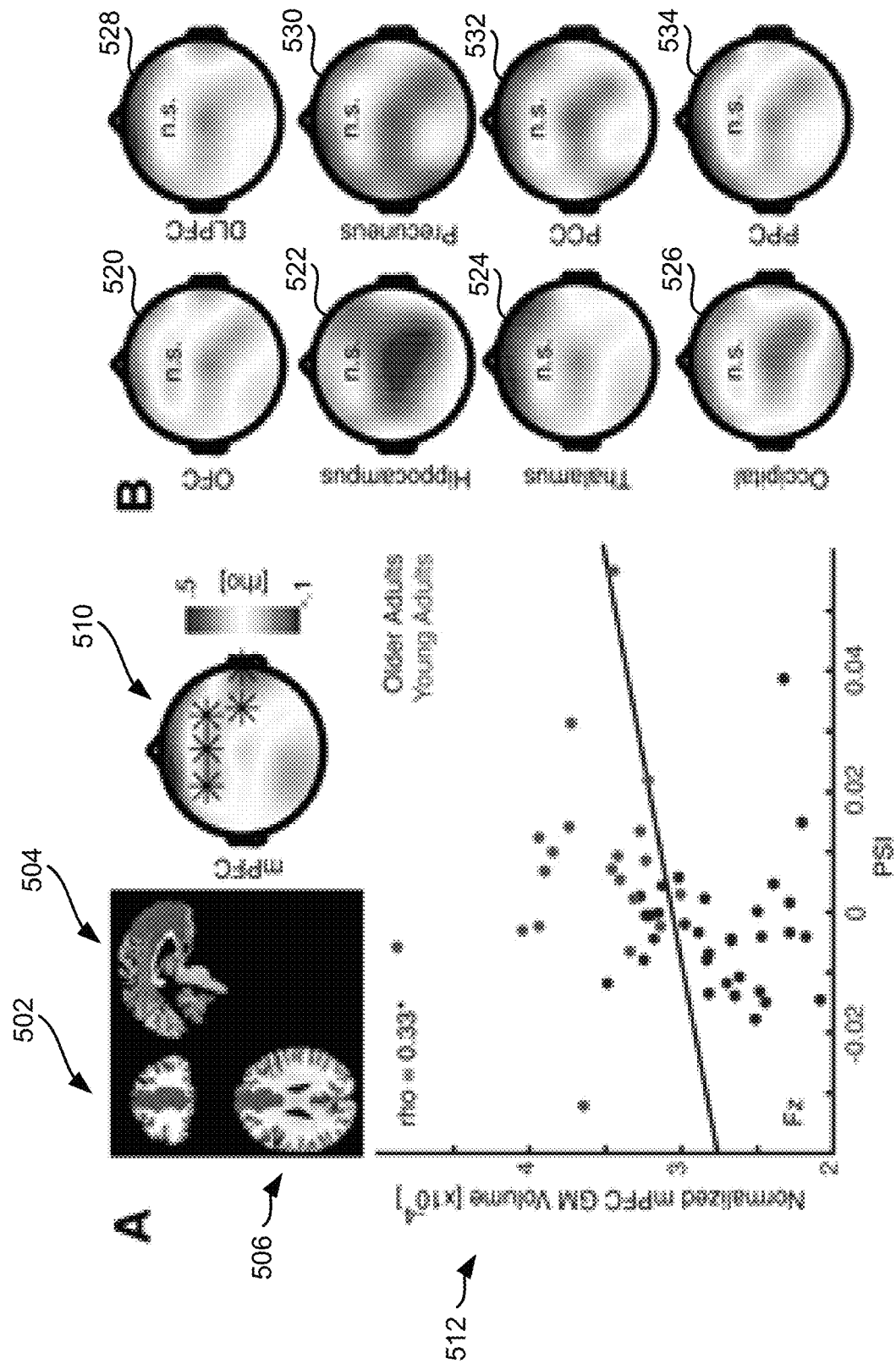
FIGS. 5A-5B illustrate dependency of directional SO-spindle coupling on prefrontal grey matter volume, in accordance with some embodiments.
Figure 6:
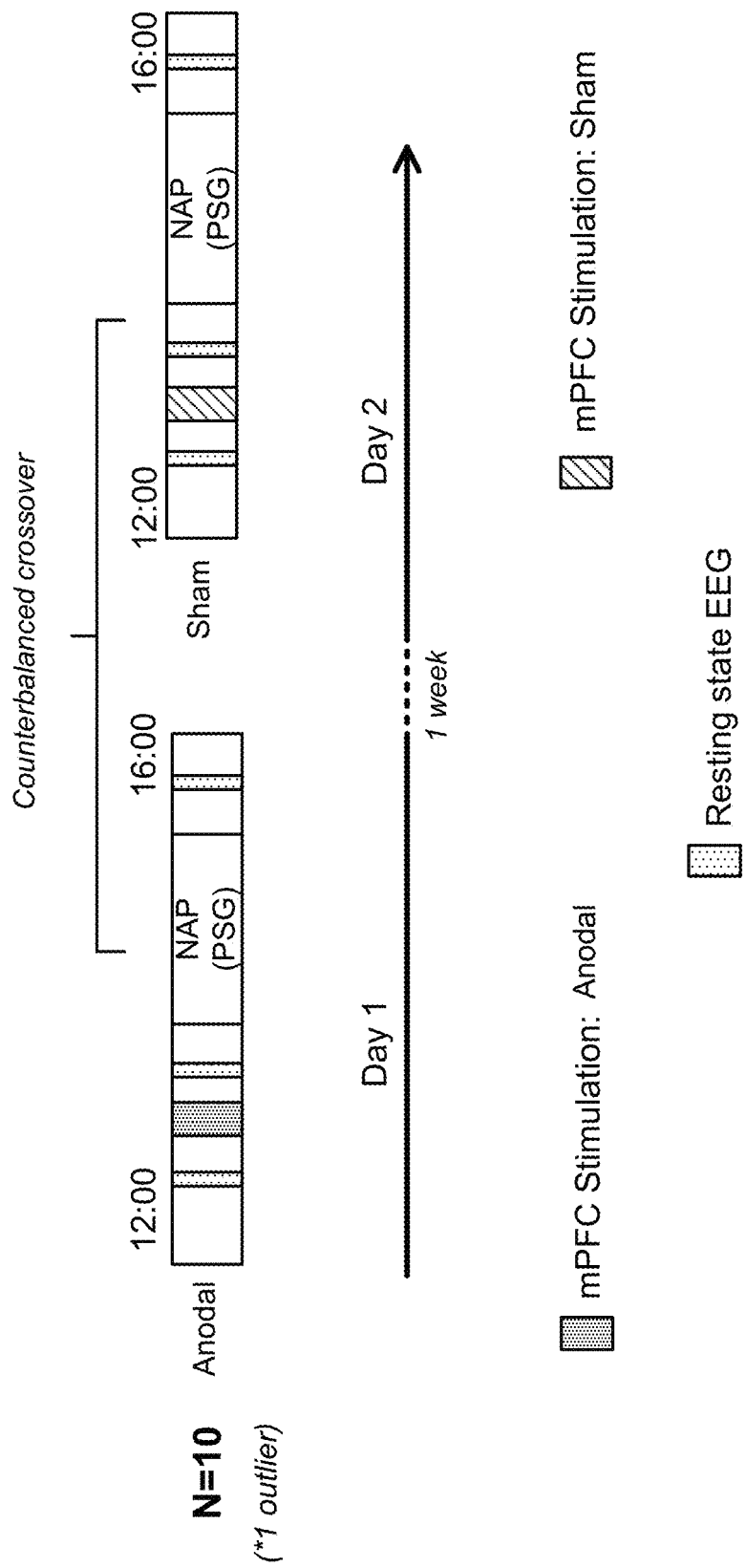
FIGS. 6-11 illustrate brain stimulation used to enhance sleep and facilitate awakening, in accordance with some embodiments.

Grey matter volume was extracted for all regions of interest (ROI) where sleep related oscillations are thought to emerge: hippocampus and the thalamus, in addition to the neighboring lateral orbitofrontal cortex (OFC) or dorsolateral PFC (DLPFC) and several control ROIs (occipital, precuneus, posterior cingulate cortex and posterior parietal cortex), but no significant effects were observed for these other eight ROIs (FIG. 5B). These results confirmed the key role of mPFC in altered SO-spindle coupling—an anatomical-physiological relationship that was not observed for other likely candidate regions.

Together, our results provide the first demonstration that: 1) the precisely coordinated timing between the cortical NREM SO 'up-state' and the sleep spindle predicts successful hippocampus-dependent memory consolidation; 2) Temporal disruption of this coordinated NREM oscillation coupling in older relative to young adults predicts impaired hippocampus-dependent overnight memory consolidation; and 3) One pathological mechanism associated with impairment in spatiotemporal coupling of the cortical SO with sleep spindles in older adults is the severity of mPFC gray matter atrophy.

Additional details are now provided regarding FIGS. 5A-5B which illustrate that directional SO-spindle coupling depends on prefrontal grey matter volume. FIG. 5A illustrates in the upper left: Definition of the mPFC ROI on coronal 502, sagittal 504 and axial 506 slices. FIG. 5A also illustrates in the upper right: Topographic map 510 of cluster-corrected correlation analysis between grey matter (GM) volume and the directional CFC (PSI), which revealed that directional influences were stronger when subjects' had more GM volume. In the lower panel, FIG. 5A illustrates a scatter plot 512 of significant correlation at electrode Fz. Hence, age-related GM atrophy might lead to a breakdown of SO-mediated spindle coupling. Note that GM volume was corrected for age-related total intracranial volume. FIG. 5B illustrates a relationship that was limited to mPFC, and was not observed in other select regions including the hippocampus 522, thalamus 524, adjacent regions such as the OFC 520 and DLPFC 528, nor in any of additional control regions (occipital 526, precuneus 530, posterior cingulate 532 and posterior parietal 534).

The Oscillatory Hierarchy of Sleep-Dependent Memory Consolidation:

A long-standing proposal in models of sleep-dependent hippocampus-dependent memory consolidation involves the timed interactive coupling between SO and sleep spindles. Indirect evidence to date has involved demonstrating that individual properties of SO and sleep spindles are linked to successful overnight memory retention. Seminal intracranial EEG studies have further highlighted the hierarchical coupling of cortical SO, cortico-thalamic sleep spindles, and hippocampal ripples. However, no assessment of memory was performed in these studies, leaving the functional relevance of these coupled NREM oscillation relationships has remained unclear. Moreover, no direct assessment of the directionality of the coupling of these events has been reported.

Here, these issues are addressed using directional cross-frequency coupling analyses, and determined how SO modulate sleep spindle timing, amplitude, and peak frequency. Our results reveal a unique spatiotemporal profile of the coupling relationship between SO and sleep spindles in young adults, such that sleep spindle amplitude peaked around the cortical 'up-state'. Moreover, this precise temporal relationship was especially pronounced over centro-parietal regions—of topographical relevance as it may be considered the anatomical convergence zone between the known frontal dominance of the SO and the parietal dominance of broad-range (11-16 Hz) spindles.

A second key finding revealed by the current study is that the normally precise spatiotemporal coordination of the SO-spindle coupled event is impaired in older adults. Unlike young adults, in which spindle events expressed a strong coincidence with the cortical SO 'up-state', spindle oscillations in older adults arrived, on average, further away from the depolarizing upswing of the SO cycle, occurring prior to it rather than just after the depolarization envelop. In addition, this phase coupling was more dispersed over SO in older adults. These findings provide evidence that the aging brain loses the neurophysiological ability to coordinate the two dominant oscillations of NREM sleep, in stark contrast to the precise spatiotemporal coupling expressed in young adults. However, these data alone do not necessarily establish that this dynamic coupling profile is of functional benefit in young adults, and whether coupling impairments in older adults is detrimental for older adults. This issue is addressed next.

SO-Spindle Coupling and Overnight Memory Consolidation:

System consolidation theory suggests that new memories are transiently more dependent on the hippocampus and then gradually transform to become more prefrontal-dependent. Endogenous NREM oscillatory activity is thought to provide the key functional substrate of timed information transfer between cortical regions. In particular, neocortical SO are thought to orchestrate thalamo-cortical sleep spindle and hippocampal ripple activity during NREM sleep to facilitate the information transfer between neocortical and hippocampal circuits. This nesting of multiple frequency bands constitutes an oscillatory hierarchy, providing the precise intrinsically-generated timing to route information from the hippocampus to neocortical areas at times of high excitability, which in turn facilitate long-term storage.

Several studies have inferred a role of the phase of the SO in determining the success of memory consolidation using indirect measures. In addition, brain stimulation studies have established that entrainment of SO can have reciprocal effects on sleep spindles, and vice versa. Most recently, it has been suggested that shifts in the exact SO-spindle timing could give rise to the behavioral benefits of electrical stimulation observed in rodents, which may also be beneficial in cognitively impaired older individuals. Our results provide the first direct evidence that the exact timing of SO and sleep spindles in the healthy, human brain significantly predicts the success of overnight hippocampus-dependent memory retention.

A further novel discovery of the current study is the demonstration that the precise temporal interplay of SO and sleep spindles is disrupted in older adults, wherein sleep spindles were misaligned (often occurring too early in the SO cycle) relative to the precise timing in young adults. The process of human brain aging appears to weaken the otherwise robust NREM oscillatory hierarchy, reducing the optimal SO-spindle phase timing, and in doing so, predicts impaired memory consolidation. Two points are of relevance in this regard. First, the finding that the memory-SO-spindle coupling relationship was significant in older adults, but at an earlier phase, importantly demonstrates that both SO and sleep spindles were still expressed in older adults. However, the mechanism that couples them in time is impaired, with spindles systematically arriving too early within the SO cycle. Second, it establishes that this impaired SO-spindle temporal coupling diminished the magnitude of overnight memory consolidation benefit.

Neurophysiological Correlates of Age-Related Memory Decline:

A multitude of studies demonstrated that aging affects sleep architecture and memory. However, no neurophysiological mechanism has been identified that functionally links age-related changes in sleep physiology to impaired memory retention, beyond quantitative reductions in the amount of oscillatory activity. Here, evidence is provided that addresses this mechanistic gap in understanding, demonstrating the loss of temporal SO-spindle coupling over specific topographical regions explains the degree of failed of memory consolidation.

Interestingly, when only focusing on the basic phase measure, sleep spindles lock as precisely to the rising flank of the SO in older adults as they do young adults, as shown in FIGS. 3C and 3D. However, our directional phase analyses revealed the existence of a clear age-related deficit. Specifically, inspection of SO-spindle interactions, shown in FIG. 3G, demonstrated that the directional influence of SO on sleep spindle timing was diminished in older adults relative to young adults, resulting in a misaligned arrival of the spindle relative to the SO. Moreover, this age-related impairment was found to be not equivalent across all brain regions, but was expressed most significantly over prefrontal cortex sensors and less strongly over parieto-occipital regions (FIG. 3G). These results further establish that, in later adult life, the human adult brain experiences a decline in the ability to precisely coordinate SO with cortico-thalamic sleep spindles. Specifically, spindles are more often expressed at unfavorable SO phases in older adults, arriving too early to confer optimal hippocampus-dependent memory consolidation benefits.

One testable hypothesis in animal models emerging from our findings is that the impaired coordination of temporal SO-spindle coupling over prefrontal cortex does not trigger hippocampal ripples as effectively, and that the magnitude of that failure should predict the consequential degree of impaired rather than successful sleep-dependent memory consolidation.

Prefrontal Atrophy, SO-Spindle Coupling and Aging:

Beyond impairments in memory-relevant SO-spindle coupling in older relative to young adults, it was further established that at least one pathological alteration contributing to the severity of this age-related coupling dysfunction—grey matter atrophy within the mPFC. Grey matter volume of the medial prefrontal cortex predicts inter-individual differences in the quality of SO in both young and older adults. Moreover, high-density EEG evidence has defined a role for the mPFC in the generation of slow waves.

Our findings advance this anatomical-neurophysiological connection. It was shown that the decrease in structural integrity of the mPFC accounts for the qualitative degree of impaired temporal phase coupling between the SO and sleep spindles. Thus, mPFC atrophy, in addition to reducing SO incidence and intensity, contributes to misalignment of the timing of sleep spindles relative to the SO phase. This effect is greatest over frontal EEG derivations, indicating that the mPFC may play a particularly important role in the regulation of the coordinated timing of NREM sleep oscillations The results reveal that the structural integrity of mPFC is one factor determining the capacity of the human brain to precisely and optimally coordinate the timed arrival of sleep spindles with the SO, and in doing so, dictate the success or failure of hippocampus-dependent memory consolidation. Intracranial studies taking advantage of invasive recordings from multiple regions of interest in concert, such as mPFC, the hippocampus, and thalamus will help to clarify the directional influences of cortical-subcortical interaction not possible with scalp EEG recordings. Such recordings occurring combined with sleep-dependent memory tasks would further our current understanding of the coordinated interactions between the mPFC, thalamus, and hippocampus that occurs during NREM sleep oscillations, as well as their necessity and sufficiency in supporting long-term memory retention.

Our findings reveal a fundamental neurophysiologic mechanism involving the spatiotemporal coupling between the SO and the sleep spindle, and demonstrate that this temporal synchrony is functionally and behaviorally relevant for the success of overnight memory consolidation. It was further shown that this same neurophysiological oscillatory dynamic is impaired in older relative to young adults, leading to imprecise sleep spindle expression in relationship with the depolarizing 'up-state' of the SO. Moreover, our findings reveal that age-related prefrontal gray matter atrophy represents one neuropathological substrate explaining the attenuation of this oscillatory control mechanism, which thus impairs hippocampus-dependent memory consolidation.

Our results are of potential clinical relevance in two ways. First, they document the presence of an under-appreciated pathway—impaired temporal precision of sleep oscillation coupling—that contributes to memory decline in later life. Second, they help define sleep oscillatory synchrony as a novel therapeutic target for modulation of hippocampus-dependent memory consolidation in older adults, and potentially in those with mild cognitive impairment and Alzheimer's disease. This may be achieved using non-invasive entrainment by means of acoustic, electric, or magnetic brain stimulation, aiming to restore the temporally precise SO-spindle coordination closer to that of young adults, helping reduced the impact of cognitive decline in aging.

Additional details are provided regarding related experimental models and subjects.

Participants:

32 healthy older (mean age: 73.7±5.3; mean±SD) and 20 younger adults (20.4±2.0 years) participated in the study. All participants provided written informed consent according to the local ethics committee (Berkeley Committee for Protection of Human Subjects Protocol Number 2010-01-595) and the Declaration of Helsinki. Data from a subset of participants has been reported previously.

Experimental Design and Procedure:

All participants were trained on the episodic word-pair task in the evening and performed a short recognition test after 10 min. Then, participants were offered an 8 h sleep opportunity, starting at their habitual bedtime. Polysomnography was collected continuously. Participants performed a long version of the recognition test approximately 2 h after awakening. Subsequently, structural MRI scans were obtained from all participants. Two older adults did not complete behavioral testing, and two young adults failed to achieve criterion at encoding. Thus, these four subjects were excluded from behavioral analyses, but were included in all electrophysiological and imaging analyses.

Behavioral Task:

A previously established sleep-dependent episodic memory task (FIG. 2A) was utilized, where subjects had to learn word-nonsense word pairs. In brief, words were 3-8 letters in length and drawn from a normative set of English words, while nonsense words were 6-14 letters in length and derived from groups of common phonemes. During encoding, subjects learned 120 word-nonsense pairs. Each pair was presented for 5 s. Participants performed the criterion training immediately after encoding. The word was presented along with the previously learned nonsense word and two new nonsense words. Subjects had to choose the correctly associated nonsense words and received feedback afterwards. Incorrect trials were repeated after a variable interval, and were presented with two additional new nonsense words to avoid repetition of incorrect nonsense words. Criterion training continued until correct responses were observed for all trials.

During recognition, a probe word or a new (foil) probe word was presented along with 4 options: (1) the originally paired nonsense word, (2) a previously displayed nonsense word, which was linked to a different probe (lure), (3) a new nonsense word or (4) an option to indicate that the probe is new. During the recognition test after a short delay (10 min), 30 probe and 15 foil trials were presented. At the long delay (10 h), 90 probe and 45 foil trials were tested. All probe words were presented only once during recognition testing, either during short or long delay testing Sleep Monitoring and EEG Data Acquisition:

Polysomnography (PSG) sleep monitoring was recorded on a Grass Technologies Comet XL system (Astro-Med), including 19-channel electroencephalography (EEG) placed using the standard 10-20 system as well as Electromyography (EMG). Electrooculogram (EOG) was recorded the right and left outer canthi. EEG recordings were referenced to bilateral linked mastoids and digitized at 400 Hz in the range from 0.1-100 Hz. Sleep scoring was performed according to standard criteria in 30 s epochs. Slow wave sleep (SWS) was defined as NREM stages 3-4, while NREM sleep encompassed stages 2-4. Given that stage 2 does not always exhibit pronounced SO activity (FIGS. 2C and 2D), the study focused on SWS for all correlational analyses.

MRI Data Acquisition:

Scanning was performed on a Siemens Trio 3T scanner with a 32-channel head coil. Two high-resolution T1-weighted anatomical images were obtained, which were acquired using a three-dimensional MPRAGE protocol with the following parameters: repetition time, 1900 ms; echo time, 2.52 ms; flip angle, 9°; field of view, 256 mm; matrix, 256×256; slice thickness, 1.0 mm; 176 slices. MPRAGE images were co-registered, and the mean image was used to perform optimized voxel-based morphometry (VBM) to examine grey matter volume within specified regions of interest (ROI) as described below.

Additional details are provided regarding quantification and statistical analysis.

Behavioral Data Analysis:

Memory recognition was calculated by subtracting both the false alarm rate (proportion of foil words, which subjects' reported as previously encountered) and the lure rate (proportion of words that were paired with a familiar, but incorrect nonsense word) from the hit rate (correctly paired word-nonsense word pairs). Memory retention was subsequently calculated as the difference between recognition at long minus short delays.

EEG Data:

Preprocessing: EEG data were imported into EEGLAB and epoched into 5 s bins, which were visually inspected for artifacts. Then the continuous data was exported to FieldTrip for further analyses.

Spectral analysis: (1) To obtain the average power spectra (FIG. 2B), the raw data was epoched into non-overlapping 15 second segments and epochs containing artifacts were rejected. Data was tapered with a Hanning window and spectral estimates were calculated from 0.5 to 50 Hz in 0.5 Hz steps and averaged per subject and channel for all epochs in NREM sleep. (2) To obtain a continuous time-frequency representation of a whole night of sleep (FIGS. 2C and 2D), multitaper spectral analyses were utilized, based on discrete prolate slepian sequences. The raw data was epoched into 30 second long segments, with 85% overlap. Spectral estimates were obtained between 0.5 and 30 Hz in 0.5 Hz steps. 29 tapers were utilized, providing a frequency smoothing of ±0.5 Hz.

Event detection: Event detection (FIG. 2D and FIGS. 3A and 3C) was performed for every channel separately based on previously established algorithms. (1) Slow oscillations: In brief, the continuous signal between 0.16 and 1.25 Hz were first filtered and all the zero crossings were detected. Then events were selected based on time (0.8-2 s duration) and amplitude (75% percentile) criteria. Finally, artifact-free 5 s long segments (±2.5 s around trough) were extracted from the raw signal. (2) Sleep spindles: The signal between 12-16 Hz was filtered and the analytical amplitude was extracted after applying a Hilbert transform. The amplitude was smoothed with a 200 ms moving average. Then the amplitude was thresholded at the 75% percentile (amplitude criterion) and only events that exceeded the threshold for 0.5 to 3 s (time criterion) were accepted. Artifact-free events were then defined as 5 s long sleep-spindle epochs (±2.5 s), peak-locked. Given that prominent power differences were observed between young and older adults (FIG. 2B), events per subjects were normalized by means of a z-score prior to all subsequent analyses, unless stated otherwise (FIG. 3A). The mean and standard deviation were derived from the unfiltered event-locked average time course of either SO or spindle events (e.g. FIGS. 2C and 2D; lower right) in every participants. Z-scores were then computed for all trials and time points.

Event-locked spectral analysis: Time-frequency representations for artifact-free normalized SO (FIG. 3B) were calculated after applying a 500 ms Hanning window. Spectral estimates (0.5-30 Hz; 0.5 Hz steps) were calculated between −2 and 2 s in steps of 50 ms and baseline-corrected by means of z-score relative to a bootstrapped baseline distribution that was created from all trials (baseline epoch −2 to −1.5 s, 10000 iterations).

Event-locked cross-frequency coupling: For event-locked cross-frequency analyses, we first filtered the normalized SO trough-locked data (FIGS. 3D and 3E; spindle-locked in FIGS. 2C and 2D) into the SO component (0.1-1.25 Hz) and extracted the instantaneous phase angle after applying a Hilbert transform. Then we filtered the same trials between 12-16 Hz and extracted the instantaneous amplitude from the Hilbert transform. We only considered the time range from −2 to 2 s to avoid filter edge artifacts. For every subject, channel, and epoch, we now detected the maximal sleep spindle amplitude and corresponding SO phase angle. The mean circular direction and resultant vector length across all NREM events were determined using the CircStat toolbox. In addition, we divided the SO phase into 17 linearly spaced bins and calculated the mean sleep spindle amplitude per bin. We normalized the individual sleep spindle amplitude distribution by the mean across all bins.

Data-driven cross-frequency coupling: We calculated a comodulogram on 15-second artifact-free long non-overlapping z-normalized segments during NREM sleep. We calculated the modulation index between lower (0.5-6.5 Hz; 0.5 Hz steps) and faster frequencies (8-40 Hz; 1 Hz steps). For the low frequency, we utilized a window of ±1 Hz, which was adjusted for the lowest frequencies. For faster frequencies, the window was adjusted to capture the side peaks. Hence, the window at a given frequency was always defined as the low center frequency+1 Hz. I.e. at 15 Hz, the window to assess coupling to the 3 Hz phase was ±4 Hz; while at 5 Hz the window was ±6 Hz. The modulation index was normalized by a bootstrapped z-score relative to a distribution that was obtained by random-point block-swapping (200 iterations).

Cross-Frequency Directionality Analysis:

To determine whether low frequencies components drive sleep spindle activity during SWS or vice versa, we calculated the cross-frequency phase slope index between the normalized signal and the signal filtered in the sleep spindle range (12-16 Hz). To avoid edge artifacts, we restricted this analysis to ±2 seconds around the SO trough. Hence, these 4 second long segments include at least 3 cycles of the SO oscillation (~0.75 Hz), in accordance with previous reports. We considered frequencies between 0.5 and 4 Hz (0.5 Hz steps; 0.25 Hz bandwidth) after applying a Hanning window and extracting the complex Fourier coefficients. Significant values above zero indicate that SO drive sleep spindle activity, while negative values indicate that sleep spindles drive SO. Values around zero indicate no directional coupling. We repeated this analysis based on 15 second long segments, which were then averaged across all available NREM events to demonstrate that the findings are not confounded by the chosen window length.

Detection of SO and Spindle Frequency Peaks:

(1) SO peak frequency (related to FIG. 2B): In order to disentangle the true oscillatory SO component from the prominent 1/f slope, we utilized irregular-resampling auto-spectral analysis (IRASA; Wen and Liu, 2016). We analyzed non-overlapping 15 s segments of continuous artifact-free data during NREM sleep and assessed frequencies between 0.1 and 30 Hz. IRASA takes advantage of the fact that irregularly resampling of the neuronal signals by pairwise non-integer values (resampling factor rf and corresponding factor rf*: e.g. 1.1 and 0.9) slightly shifts the peak frequency of oscillatory signals by compressing or stretching the underlying signal. However, the 1/f component remains stable. This procedure is then repeated in small, overlapping windows (window size: 5 s, sliding steps: 1 s; resampling factors rf: 1.1-1.9 in 0.05 increments). Note resampling was always done in a pairwise fashion for factor h and the corresponding resampling factor rf*=2−rf. For each segment, we calculated the auto-power spectrum by means of a FFT after applying a Hanning window. Then all auto-spectra were median-averaged to obtain the power spectrum of the 1/f component, with the idea being that resampled oscillatory components are averaged out. Finally, the resampled 1/f PSD is subtracted from the original PSD to obtain the oscillatory residuals on which we performed the individual peak detection (SO range: peak <2 Hz; spindle-range: 9-17 Hz).

(2) In addition to IRASA, which provides a mean sleep spindle peak frequency, we also utilized a linear de-trending approach to assess spindle frequencies as a function of the SO phase (FIG. 4C), where we investigated whether SO modulates additional sleep spindle features besides the amplitude on a fine-grained temporal scale. Therefore, we screened every artifact-free normalized SO event (−1.25 to 1.25 around trough) at every channel separately for oscillatory activity in the sleep spindle range. First, we zero-padded every trial to 10 seconds to increase the frequency resolution (0.1 Hz), then applied a Hanning window and obtained spectral estimates between 8 and 16 Hz. The resulting power values were log transformed. The sleep spindle peak for every SO was detected after subtraction of linear fit to the spectrum to remove the 1/f component. Second, every trial was filtered at the trial-specific peak frequency (±2 Hz) and the instantaneous amplitude was extracted from a Hilbert transform before we performed event-related cross-frequency coupling analyses. In addition, we only considered SO that contained sleep spindle events that exceeded the 75% percentile of sleep spindle amplitudes to ensure comparability for correlation analyses. This approach effectively corrected for differences in sleep spindle peak frequencies and spectral power distributions prior to correlation with behavior. To obtain time-resolved sleep spindle peak frequency estimates, the sleep spindle peak was detected as described above in a 500 ms sliding window approach. The window in 25 ms steps was shifted relative to the SO events (−1 to 1 s; ±250 ms) and recalculated the sleep spindle peak frequency. Finally, the resulting traces were smoothed with 100 ms moving average.

Structural MRI Data Analysis:

To measure grey matter volume, optimized voxel-based morphometry (VBM) was performed using SPM8 with the VBM8 toolbox and the Diffeomorphic Anatomical Registration through Exponentiated Lie algebra (DARTEL) toolbox in order to improve registration of older brains to the normalized MNI template. To enhance signal to noise ratio, two T1-weighted MPRAGE images were first co-registered and averaged. Averaged images were then segmented applying the Markov random field approach and then registered, normalized, and modulated using DARTEL. Grey matter and white matter segmentations were inputted into DARTEL and utilized to create a study specific template, which was then used to normalize individual brains into MNI space. Modulated grey matter maps were then smoothed using an 8 mm Gaussian kernel.

Measures of total intracranial volume (TIV) for each participant were estimated from the sum of grey matter, white matter, and CSF segmentation, and then used to adjust grey matter volumetric measures to account for differences in head size. Given that slow oscillations, sleep spindles, and ripples depend on the interaction between prefrontal cortex, thalamus, and hippocampus regions, the Anatomical Automatic Labeling repository within the Wake Forest University PickAtlas toolbox was used to generate anatomically-based ROIs for the hippocampus, thalamus, medial prefrontal cortex, and orbitofrontal cortex, as well as an occipital lobe control ROI. Mean voxelwise gray matter volume within anatomically defined ROIs were extracted using the Marsbar toolbox and used in analyses relating grey matter volumetric measures with sleep and memory variables.

Statistical Analysis:

Unless stated otherwise, cluster-based permutation tests were used to correct for multiple comparisons as implemented in FieldTrip (Monte Carlo method; 1000 iterations; maxsize criterion). Clusters were formed in time/frequency (e.g. FIGS. 3B and 3F) or space (e.g. FIGS. 3E and 3G) by thresholding independent t-tests (e.g. FIGS. 3E-G), circular-linear (e.g. FIGS. 4A and 4D) or linear correlations (Spearman, e.g. FIG. 5A) at p<0.05. Correlation values were transformed into t-values. A permutation distribution was then created by randomly shuffling labels. The permutation p-value was obtained by comparing the cluster statistic to the random permutation distribution. The clusters were considered significant at p<0.05 (two-sided). Bonferroni-correction was applied to correct for multiple cluster tests (e.g. FIG. 5B).

Circular statistics were calculated using the CircStat toolbox. Circular non-uniformity was assessed with Rayleigh tests at p<0.01. Effect sizes were quantified by means of Cohen's d, the correlation coefficient rho or η2 in case of repeated measures ANOVAs or Watson-Williams-tests (circular ANOVA equivalent). Circular-linear correlations were calculated according to the following equations 1-4:

$$\rho = \sqrt{\frac{r_{xs}^2 + r_{xc}^2 - 2 * r_{xs} * r_{xc} * r_{cs}}{1 - r_{cs}^2}} \quad (1)$$

In various embodiments, $r_{xs}$, $r_{xc}$ and $r_{cs}$ were defined as $$r_{xs} = \mathrm{corr}(x, \sin(\mathrm{alpha})) \quad (2)$$

$$r_{xc} = \mathrm{corr}(x, \cos(\mathrm{alpha})) \quad (3)$$

$$r_{cs} = \mathrm{corr}(\sin(\mathrm{alpha}), \cos(\mathrm{alpha})) \quad (4)$$

Where x is the linear and alpha being the circular variable. In order to control for confounding variables, partial correlations were utilized, where c was partialled out of x, sin(alpha) and cos(alpha) before computing the multiple correlation using the regression residuals. A threshold of 10% was utilized to define clusters following partial correlations, which were then again tested at a cluster alpha of 0.05. To obtain effect sizes for cluster tests, the effect size separately for all channel, frequency and/or time points was calculated and averaged across all data points in the cluster. Repeated-measures ANOVAs were Greenhouse-Geisser corrected.

Additional details are provided regarding FIGS. 6-11, which illustrate brain stimulation used to enhance sleep and facilitate awakening. As shown in FIGS. 6-11, N=8. As illustrated, stimulation has an effect on NREM slow activity. In various embodiments, stimulation appears to be triggering a state-specific EEG effect. Whatever the dominant frequency of the state that is observed (sleep, or just Stage 2, or just SWS, or just REM), stimulation seems to selectively increase the innate dominate rhythm of that brain state. In addition, effects are visible on gross sleep amounts in terms of time. Also visible are about a 6-8% increase in NREM SWS %. FIGS. 7-11 illustrate t stat mapsisitic differences between Stim and Sham in spectral activity bins during the PSG nap, with red colors indicating positive increases due to Stim, and blue colors indicating negative decreases due to Stim.

Figure 7:
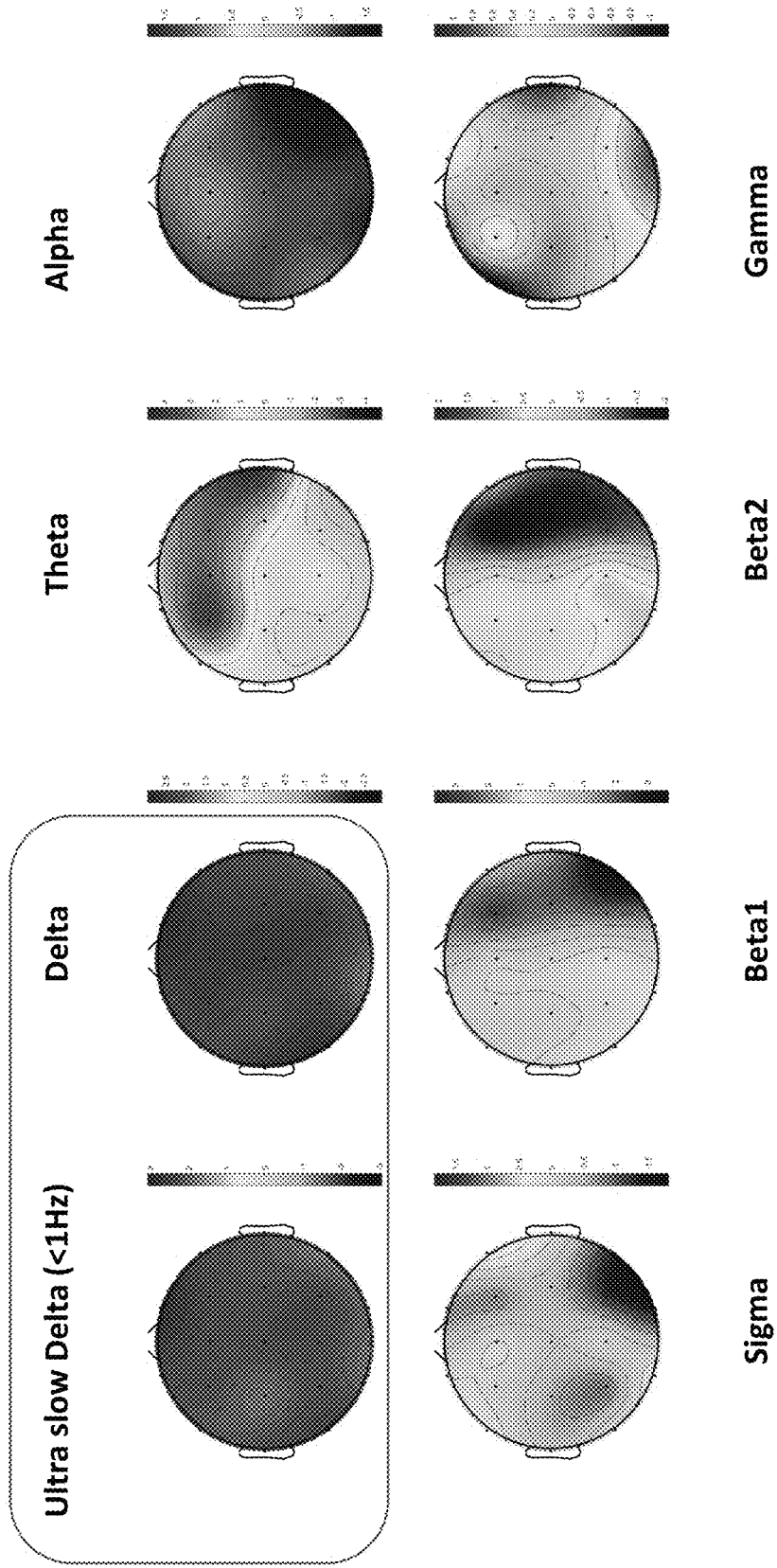

With regard to FIG. 7, illustrated are the Stim vs Sham differences for all sleep, combined (i.e., all stages combined). Note that Stim is working, such that Anodal stim before sleep is subsequently increasing the amount of Ultra slow Delta (<1 Hz) wave power, as well as general Delta (0.8-4 Hz). Also note that Stim is decreasing the overall amount of faster frequency activity, considered to be "non-restorative" sleep in terms of EEG.

Figure 8:
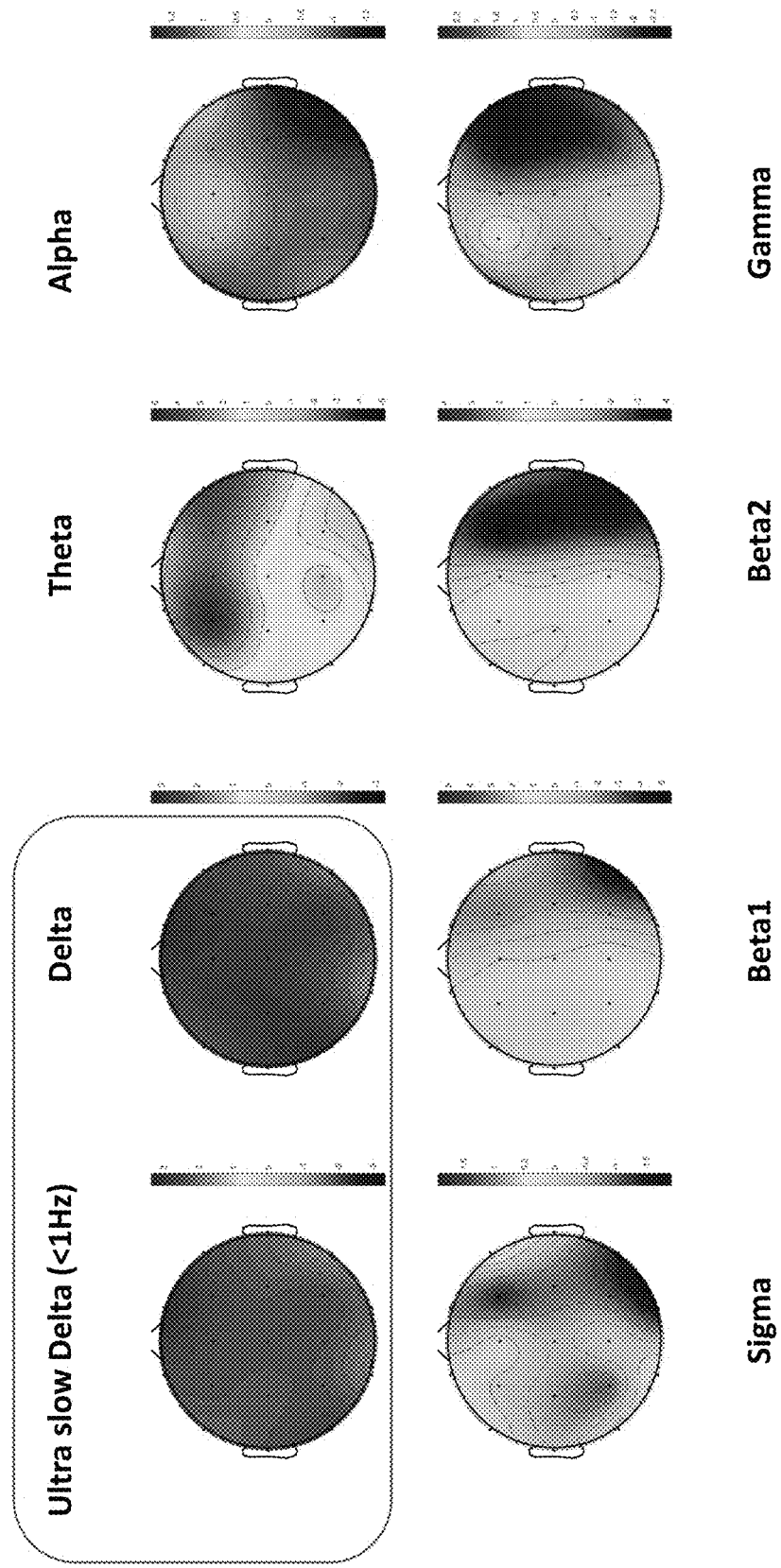

With regard to FIG. 8, illustrated are the Stim vs Sham differences for all of NREM sleep (i.e., Stage 1-4, combined). Similar to above, Stim is working such that Anodal stim before sleep is subsequently increasing the amount of Ultra slow Delta (<1 Hz) wave power, and especially general Delta (0.8-4 Hz). Also note that Stim is decreasing the overall amount of faster frequency activity, considered to be "non-restorative" sleep in terms of EEG.

Figure 9:
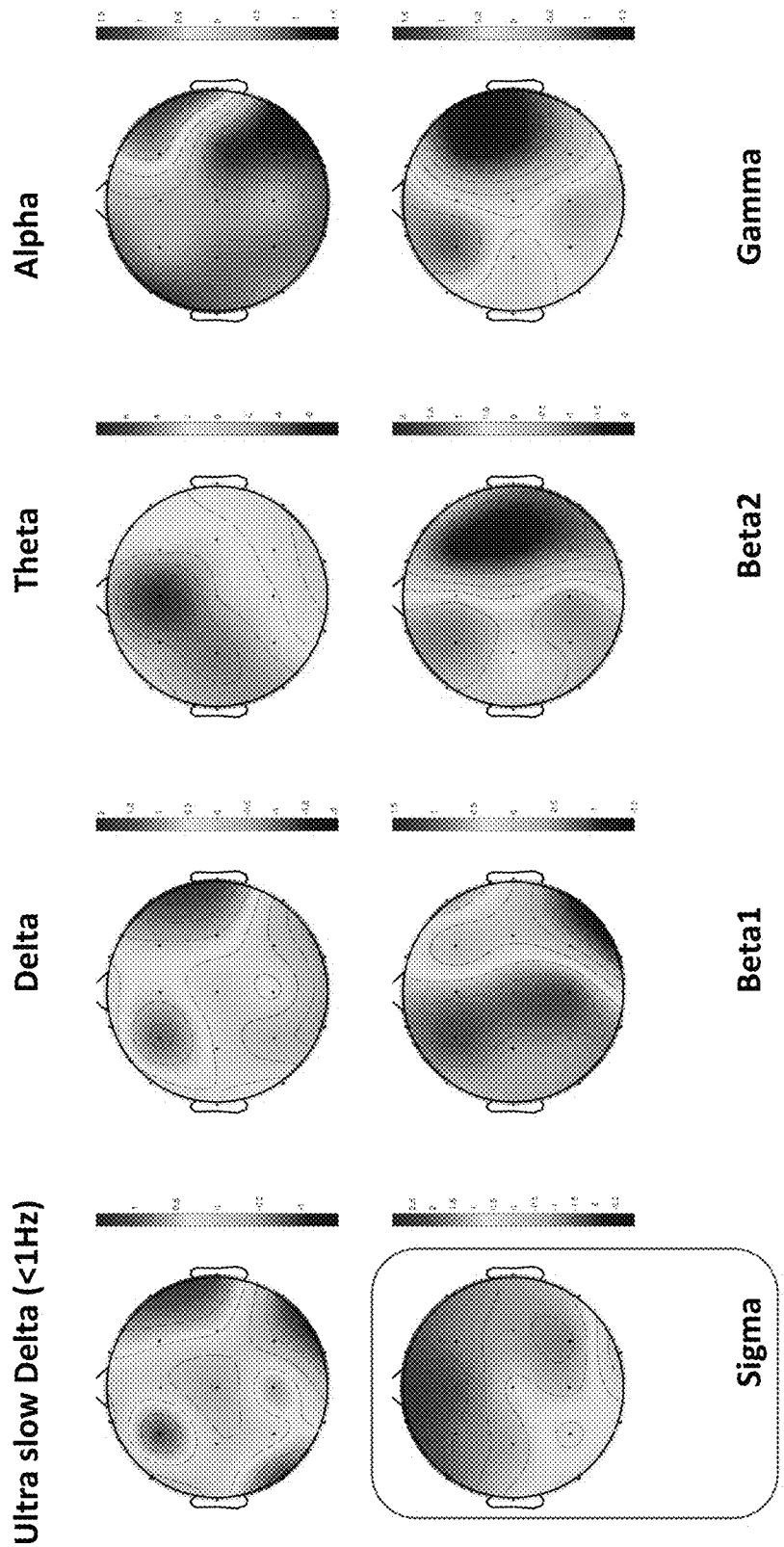

With regard to FIG. 9, illustrated are the Stim vs Sham differences for just NREM stage 2, and somewhat different to NREM or SWS. The stronger effects seen are actually for sigma activity—which is the sleep spindle range, consistent with spindles be predominantly a stage-2 phenomenon. Weaker effects are visible on decreasing overall amount of faster frequency activity.

Figure 10:
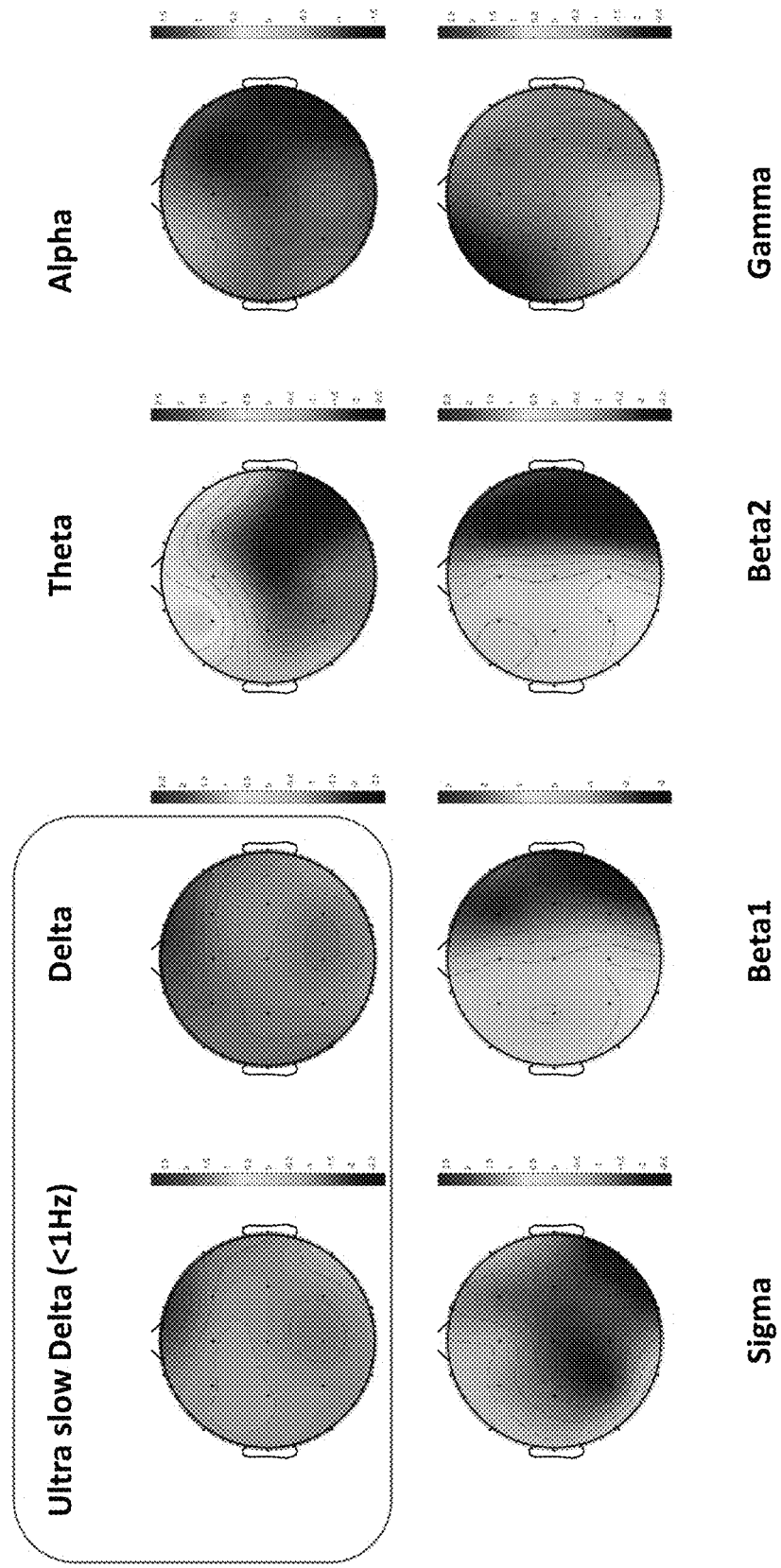

With regard to FIG. 10, illustrated are the Stim vs Sham differences for NREM and SWS (stages 3&4). Similar to above, but weaker effects are visible in slow and general delta range. Also note that Stim is decreasing the overall amount of faster frequency activity, considered to be "non-restorative" sleep in terms of EEG.

Figure 11:
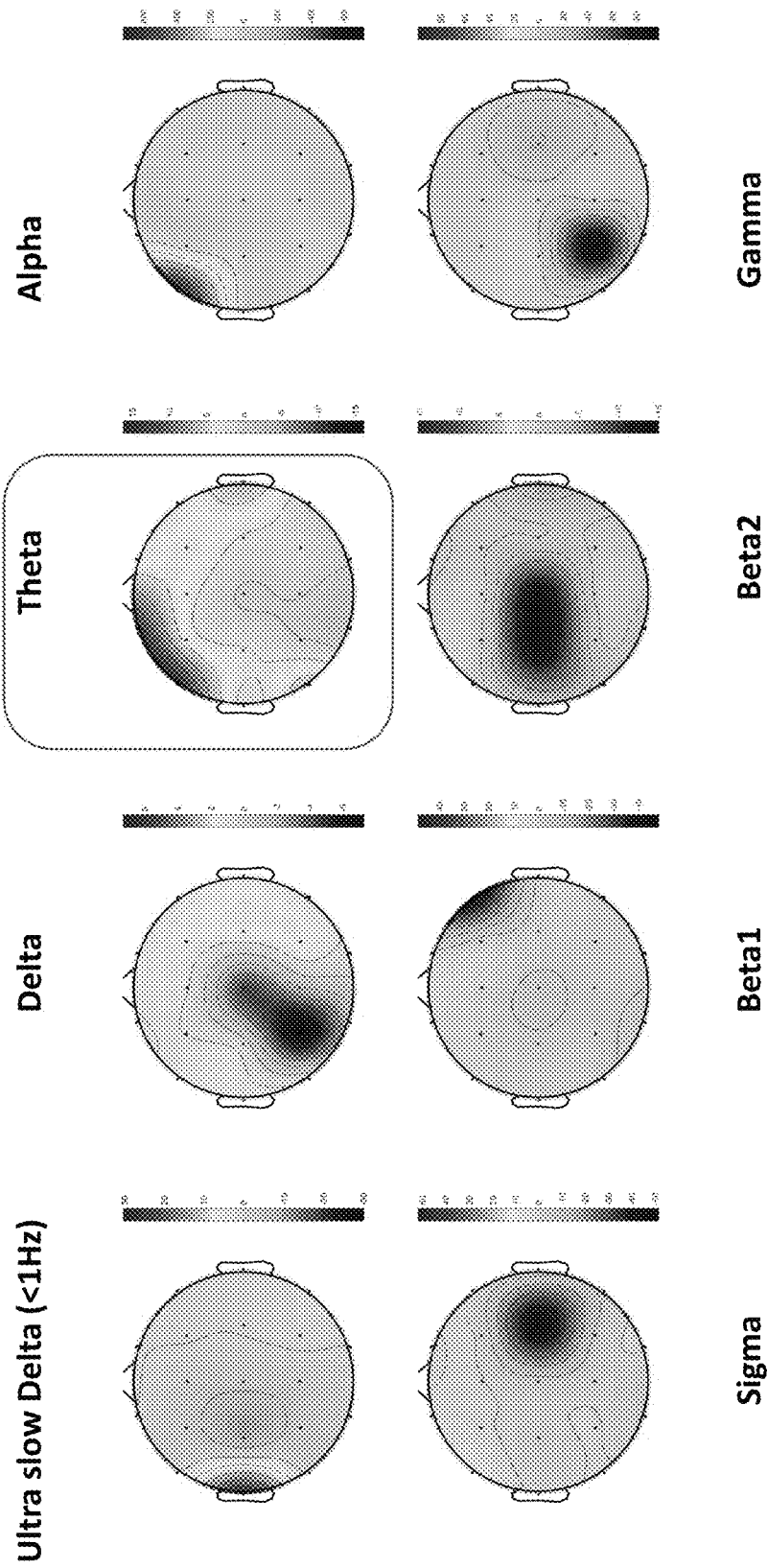

With regard to FIG. 11, illustrated are the Stim vs Sham differences for REM sleep. First, the t stats appear to be large, and aspects of the electrodes may be driving this. Also noted in FIG. 11 is that Stim seems to be increasing theta activity, which is the dominant spectral rhythm of REM sleep.

Figure 12:
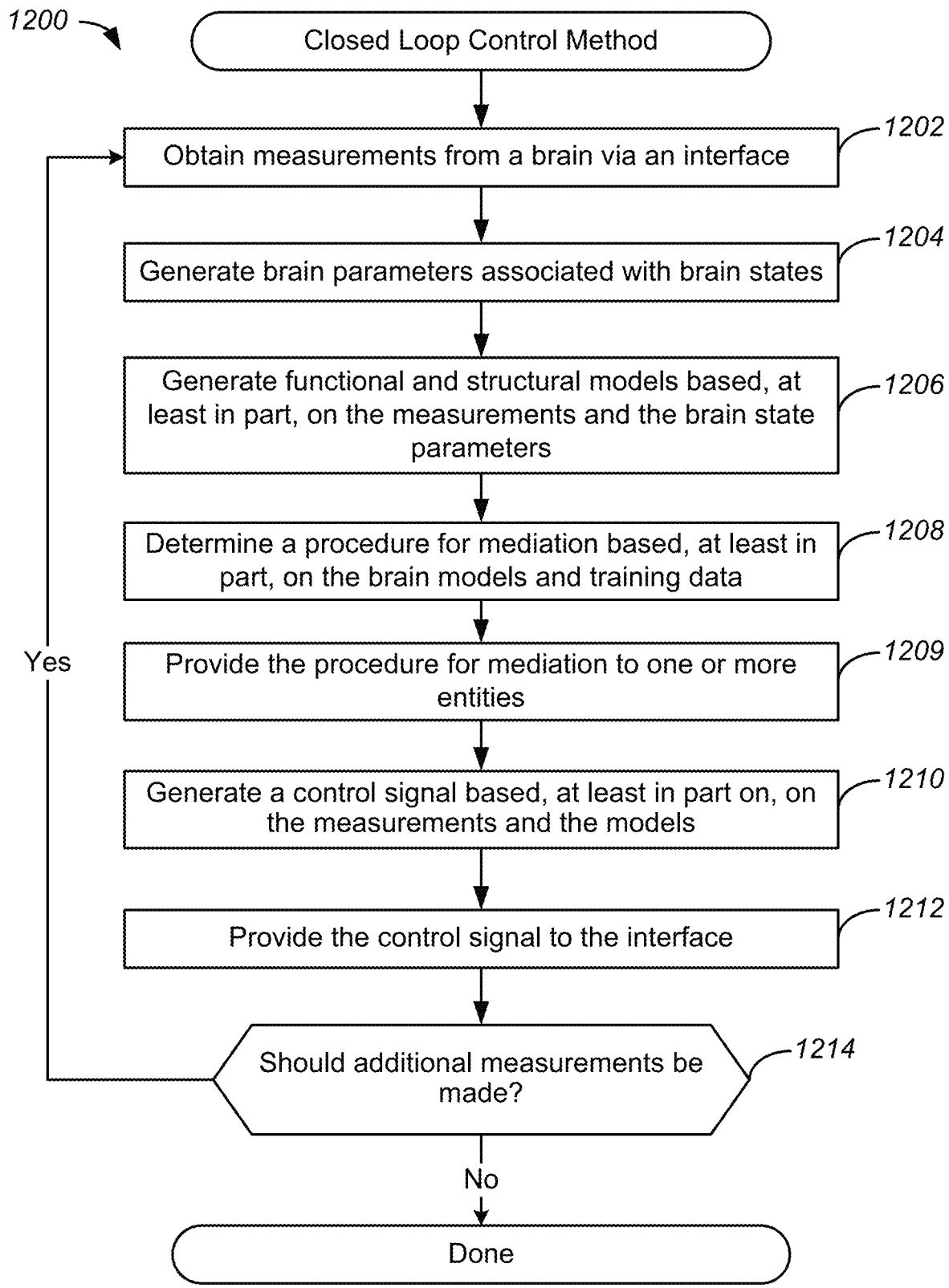
FIG. 12 illustrates a flowchart of an example of a method for providing brain monitoring and stimulation, implemented in accordance with some embodiments.

With reference to FIG. 12, shown is a flow chart of a method 1200 for providing brain monitoring and stimulation, implemented in accordance with some embodiments. As discussed above, various components of system 100 may be configured to implement modeling and closed loop management of treatments and therapies provided to a user.

Accordingly, method 1200 may commence with operation 1202 during which measurements are obtained from a brain via an interface. The measurements may represent neural activity over a particular period of time, or temporal window, and may be obtained via components of a brain interface. Such measurements may be acquired and stored in a memory. In various embodiments, the plurality of measurements includes indications of slow wave oscillations and sleep spindles as described above.

Method 1200 may proceed to operation 1204 during which parameters associated with brain states are generated. As similarly discussed above, such parameters may include observers and estimators associated with brain states as well as identification of the brain states themselves. Such brain states may include an unconscious state corresponding to NREM sleep phases. Such parameters may be generated by a first processing device and may be stored in a local memory. In particular embodiments, the brain state parameters include an indication of a synchrony pattern between the measured slow wave oscillations and the measured sleep spindles, as described above. In some embodiments, the generation of brain state parameters may include assessment of the temporal directionality of SO-spindle interactions.

Method 1200 may proceed to operation 1206 during which functional and structural models are generated based, at least in part, on the measurements and the parameters. As discussed above, such models may emulate functions, tasks, and components of the user's brain, and may be configured based on the brain's activity and behavior. Such models may also be configured based on previously obtained reference data. Such models may also be configured based on the determined synchrony pattern of measured slow wave oscillations and the measured sleep spindles.

Method 1200 may process to operation 1208 during which a procedure for mediation is determined. In some embodiments, the procedure for mediation is configured to adjust the intensity of slow wave oscillations of the subject. Such adjustments, such as increasing the slow wave oscillation intensity, may cause enhanced slow wave oscillation and spindle synchrony. In some embodiments, the models of the brain are used to determine the procedure for mediation. The models of the brain may include predicted timing of the peaks and valleys of various brain waves of the subject's brain, which may be used to determine the timing for applying mediating stimuli to such brain In some embodiments, training data is additionally used, with the training data consisting of one or more mediation data points. In some embodiments, the mediation data points include, for example, one or more models of additional users' brains, or one or more previous procedures for stimulation of brain wave oscillations. In some embodiments, the training data is used in conjunction with machine learning algorithms or artificial intelligence modalities. In some embodiments, the machine learning algorithms or artificial intelligence modalities determine a procedure for mediation based on one or more data points within the training data that are determined to suggest a procedure for mediation that adjusts intensity, frequency, or power of various brain waves. For example, if one or more data points of previous mediation of brain waves of users suggest, via machine learning algorithms that process and analyze the data points, a method that leads to optimal increase in slow wave oscillation intensity, then a procedure for mediation of the user's brain waves can be determined based on those data points.

In some embodiments, method 1200 may proceed to operation 1209 during which the procedure for mediation is provided to one or more entities. In some embodiments, the one or more entities may be, for example, client devices, user devices 110, first processing device 104, second processing device 106, controller 108, one or more external applications or websites, or some combination thereof.

Method 1200 may proceed to operation 1210 during which a control signal is generated based, at least in part on, on the measurements and the models. Accordingly, one or more control signals may be generated based on recent neural activity represented by measurement data, and also based on expected or desired effects as determined based on the models. In this way, specific control signals may be generated to implement a particular cognitive modulation that is specifically configured for the user. Moreover, as discussed above and in greater detail below, such control signals may be generated and implemented in a closed loop manner.

Method 1200 may proceed to operation 1212 during which the control signal is provided to the interface. Accordingly, the control signal may be provided to the interface which may generate one or more stimuli based on the control signal. For example, such stimuli may include electrical stimuli, visual stimuli, aural stimuli, and/or tactile stimuli that may have parameters, such as amplitude and duration, determined based on the control signal. Such stimuli, such as electrical stimuli, may be applied to the cortical tissue of the brain.

Method 1200 may proceed to operation 1214 during which it may be determined if additional measurements should be made. In various embodiments, such a determination may be made based on a current state, or in response to one or more conditions. For example, if a particular therapeutic regimen is implemented, a series of measurement may be made according to a predetermined schedule, and such measurements may be stepped through utilizing a state machine. If it is determined that additional measurements should be made, method 1200 may return to operation 1202. If it is determined that no additional measurements should be made, method 1200 may terminate.

FIG. 13 illustrates an example of a computer system or a processing device 1300 that can be used with various embodiments. For example, processing device 1300 can be used to implement interface 102, first processing device 104, second processing device 106, controller 108, client device 110, and/or prosthetic 112 according to various embodiments described above. For instance, the processing device 1302 can be used to implement brain stimulation in accordance with the various embodiments described above. In addition, the processing device 1302 shown can represent a computing system on a mobile device or on a computer or laptop, etc. According to particular example embodiments, a processing device 1302 suitable for implementing particular embodiments of the present invention includes a processor 1301, a memory 1303, an interface 1311, and a bus 1315 (e.g., a PCI bus). The interface 1311 may include separate input and output interfaces, or may be a unified interface supporting both operations. When acting under the control of appropriate software or firmware, the processor 1301 is responsible for tasks such as brain stimulation described above. Various specially configured devices can also be used in place of a processor 1301 or in addition to processor 1301. The complete implementation can also be done in custom hardware. The interface 1311 is typically configured to send and receive data packets or data segments over a network. Particular examples of interfaces the device supports include Ethernet interfaces, frame relay interfaces, cable interfaces, DSL interfaces, token ring interfaces, and the like.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the processing device 1302 uses memory 1303 to store data and program instructions and maintain a local side cache. The program instructions may control the operation of an operating system and/or one or more applications, for example. The memory or memories may also be configured to store received metadata and batch requested metadata.

Because such information and program instructions may be employed to implement the systems/methods described herein, the present invention relates to tangible, machine readable media that include program instructions, state information, etc. for performing various operations described herein. Examples of machine-readable media include hard disks, floppy disks, magnetic tape, optical media such as CD-ROM disks and DVDs; magneto-optical media such as optical disks, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

While the present disclosure has been particularly shown and described with reference to specific embodiments thereof, it will be understood by those skilled in the art that changes in the form and details of the disclosed embodiments may be made without departing from the spirit or scope of the invention. Specifically, there are many alternative ways of implementing the processes, systems, and apparatuses described. It is therefore intended that the invention be interpreted to include all variations and equivalents that fall within the true spirit and scope of the present invention. Moreover, although particular features have been described as part of each example, any combination of these features or additions of other features are intended to be included within the scope of this disclosure. Accordingly, the embodiments described herein are to be considered as illustrative and not restrictive.

What is claimed is:

1. A method comprising:
    obtaining a plurality of measurements from a brain of a user via an interface, wherein the plurality of measurements includes indications of slow wave oscillations and sleep spindles;
    generating, via a first processing device comprising one or more processors, a plurality of brain state parameters characterizing one or more features of at least one brain state of the brain of the user, wherein the plurality of brain state parameters includes an indication of a synchrony pattern between the measured slow wave oscillations and the measured sleep spindles including an assessment of a temporal directionality of interactions between the measured slow wave oscillations and sleep spindles and an amount of temporal deviation between slow wave oscillation peaks and sleep spindle peaks;
    via a second processing device comprising one or more processors,
        generating a machine learning model of the brain of the user based, at least in part, on the plurality of measurements and the synchrony pattern, and
        determining, using the machine learning model of the brain of the user and training data comprising one or more mediation data points, a procedure for mediation specifying at least an amplitude or a duration of stimuli to be applied to the brain to adjust a power of slow wave oscillations;
    generating one or more control signals, via a controller, based on the procedure for mediation, wherein the one or more control signals are transmitted to the interface; and
    generating, via the interface, one or more stimuli based on the one or more control signals, wherein the one or more stimuli is applied to cortical tissue of the brain, wherein the one or more stimuli is configured to enhance synchrony of slow wave oscillations and sleep spindles such that sleep spindle peaks occur closer to slow wave oscillation peaks.

2. The method of claim 1 further comprising:
    obtaining a plurality of subsequent measurements from the brain via the interface, wherein the plurality of subsequent measurements are obtained after the one or more stimuli is applied to the brain;
    determining, via the first processing device, changes to the plurality of brain state parameters based on the plurality of subsequent measurements;
    modifying, via the second processing device, the procedure for mediation based on the changes to the plurality of brain state parameters, wherein the procedure for mediation is updated using the machine learning model; and
    adjusting the machine learning model based on the one or more control signals and the plurality of subsequent measurements.

3. The method of claim 1, wherein the one or more stimuli is configured to increase the power of slow wave oscillations of the brain to enhance synchrony of slow wave oscillation peaks and sleep spindle peaks.

4. The method of claim 1, wherein the at least one brain state includes an unconscious state corresponding to non-rapid-eye-movement sleep.

5. The method of claim 1, further comprising providing the procedure for mediation to one or more entities.

6. The method of claim 5, wherein the one or more entities includes a client device corresponding to a medical professional.

7. A system comprising:
    an interface configured to obtain a plurality of measurements from a brain of a user, wherein the plurality of measurements includes indications of slow wave oscillations and sleep spindles;
    a first processing device comprising one or more processors configured to generate a plurality of brain state parameters characterizing one or more features of at least one brain state of the brain of the user, wherein the brain state parameters include an indication of a synchrony pattern between the measured slow wave oscillations and the measured sleep spindles including an assessment of a temporal directionality of interactions between the measured slow wave oscillations and sleep spindles and an amount of temporal deviation between slow wave oscillation peaks and sleep spindle peaks;

a second processing device comprising one or more processors configured to:
  generate a machine learning model of the brain of the user based, at least in part, on the plurality of measurements and the synchrony pattern, and
  determine, using the machine learning model of the brain of the user and training data comprising one or more mediation data points, a procedure for mediation specifying at least an amplitude or a duration of stimuli to be applied to the brain to adjust a power of slow wave oscillations; and a controller comprising one or more processors configured to generate one or more control signals based on the procedure for mediation, wherein the one or more control signals are transmitted to the interface;

wherein the interface is further configured to generate one or more stimuli based on the one or more control signals, wherein the one or more stimuli is applied to cortical tissue of the brain, wherein the one or more stimuli is configured to enhance synchrony of slow wave oscillations and sleep spindles such that sleep spindle peaks occur closer to slow wave oscillation peaks.

8. The system of claim 7,
wherein the interface is further configured to obtain a plurality of subsequent measurements from the brain, wherein the plurality of subsequent measurements are obtained after the one or more stimuli is applied to the brain;
wherein the first processing device is further configured to determine changes to the plurality of brain state parameters based on the plurality of subsequent measurements;
wherein the second processing device is further configured to:
  modify the procedure for mediation based on the changes to the plurality of brain state parameters, wherein the procedure for mediation is updated using the machine learning model, and
  adjust the machine learning model based on the one or more control signals and the plurality of subsequent measurements.

9. The system of claim 7, wherein the one or more stimuli is configured to increase the power of slow wave oscillations of the brain to enhance synchrony of slow wave oscillation peaks and sleep spindle peaks.

10. The system of claim 7, wherein the at least one brain state includes an unconscious state corresponding to non-rapid-eye-movement sleep.

11. The system of claim 7, wherein the second processing device is further configured to provide the procedure for mediation to one or more entities.

12. The system of claim 11, wherein the one or more entities includes a client device corresponding to a medical professional.

13. A non-transitory computer readable medium storing one or more programs configured for execution by a computer, the one or more programs comprising instructions for:

obtaining a plurality of measurements from a brain of a user via an interface, wherein the plurality of measurements includes indications of slow wave oscillations and sleep spindles;

generating, via a first processing device comprising one or more processors, a plurality of brain state parameters characterizing one or more features of at least one brain state of the brain of the user, wherein the plurality of brain state parameters includes an indication of a synchrony pattern between the measured slow wave oscillations and the measured sleep spindles including an assessment of a temporal directionality of interactions between the measured slow wave oscillations and sleep spindles and an amount of temporal deviation between slow wave oscillation peaks and sleep spindle peaks;

via a second processing device comprising one or more processors,
  generating a machine learning model of the brain of the user based, at least in part, on the plurality of measurements and the synchrony pattern, and
  determining, using the machine learning model of the brain of the user and training data comprising one or more mediation data points, a procedure for mediation specifying at least an amplitude or a duration of stimuli to be applied to the brain to adjust a power of slow wave oscillations;

generating one or more control signals, via a controller, based on the procedure for mediation, wherein the one or more control signals are transmitted to the interface; and generating, via the interface, one or more stimuli based on the one or more control signals, wherein the one or more stimuli is applied to cortical tissue of the brain, wherein the one or more stimuli is configured to enhance synchrony of slow wave oscillations and sleep spindles such that sleep spindle peaks occur closer to slow wave oscillation peaks.

14. The non-transitory computer readable medium of claim 13, wherein the one or more programs further comprise instructions for:
  obtaining a plurality of subsequent measurements from the brain via the interface, wherein the plurality of subsequent measurements are obtained after the one or more stimuli is applied to the brain;
  determining, via the first processing device, changes to the plurality of brain state parameters based on the plurality of subsequent measurements;
  modifying, via the second processing device, the procedure for mediation based on the changes to the plurality of brain state parameters, wherein the procedure for mediation is updated using the machine learning model; and
  adjusting the machine learning model based on the one or more control signals and the plurality of subsequent measurements.

15. The non-transitory computer readable medium of claim 13, wherein the one or more stimuli is configured to increase the power of slow wave oscillations of the brain to enhance synchrony of slow wave oscillation peaks and sleep spindle peaks.

16. The non-transitory computer readable medium of claim 13, wherein the at least one brain state includes an unconscious state corresponding to non-rapid-eye-movement sleep.

17. The non-transitory computer readable medium of claim 13, wherein the one or more programs further comprise instructions for: providing the procedure for mediation to one or more entities.

* * * * *